(12) United States Patent
Van Ginkel et al.

(10) Patent No.: US 9,132,179 B2
(45) Date of Patent: Sep. 15, 2015

(54) COMPOSITIONS FOR REDUCING BACTERIAL CARRIAGE AND CNS INVASION AND METHODS OF USING SAME

(75) Inventors: Frederik W. Van Ginkel, Auburn, AL (US); David E. Briles, Birmingham, AL (US); James M. Watt, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 1110 days.

(21) Appl. No.: 10/578,939

(22) PCT Filed: Nov. 10, 2004

(86) PCT No.: PCT/US2004/037394
§ 371 (c)(1),
(2), (4) Date: Feb. 14, 2007

(87) PCT Pub. No.: WO2005/046721
PCT Pub. Date: May 26, 2005

(65) Prior Publication Data
US 2007/0286866 A1 Dec. 13, 2007

Related U.S. Application Data

(60) Provisional application No. 60/518,799, filed on Nov. 10, 2003.

(51) Int. Cl.
| | | |
|---|---|---|
| *C07K 14/00* | (2006.01) | |
| *A61K 39/00* | (2006.01) | |
| *A61K 39/02* | (2006.01) | |
| *A61K 39/09* | (2006.01) | |
| *C07K 16/12* | (2006.01) | |
| *C07K 16/40* | (2006.01) | |
| *C12N 9/24* | (2006.01) | |
| *A61K 38/00* | (2006.01) | |

(52) U.S. Cl.
CPC ........... *A61K 39/092* (2013.01); *C07K 16/1275* (2013.01); *C07K 16/40* (2013.01); *C12N 9/2402* (2013.01); *C12Y 302/01018* (2013.01); *A61K 38/00* (2013.01); *A61K 2039/543* (2013.01); *A61K 2039/55544* (2013.01)

(58) Field of Classification Search
CPC .................................................. A61K 39/092
See application file for complete search history.

(56) References Cited

U.S. PATENT DOCUMENTS

| | | | |
|---|---|---|---|
| 5,792,457 A * | 8/1998 | Tuomanen et al. | 424/139.1 |
| 5,854,416 A * | 12/1998 | Sampson et al. | 536/23.7 |
| 6,027,734 A | 2/2000 | Briles et al. | |
| 6,312,944 B1 | 11/2001 | Russell et al. | |
| 6,420,135 B1 | 7/2002 | Kunsch et al. | |
| 6,500,613 B1 | 12/2002 | Briles et al. | |
| 6,514,503 B1 | 2/2003 | Gizurarson et al. | |
| 6,565,856 B1 | 5/2003 | Skeiky et al. | |
| 6,573,082 B1 | 6/2003 | Choi et al. | |
| 6,635,246 B1 | 10/2003 | Barrett et al. | |
| 6,699,703 B1 | 3/2004 | Doucette-Stamm et al. | |
| 6,800,744 B1 * | 10/2004 | Doucette-Stamm et al. | 536/23.1 |
| 7,202,056 B2 * | 4/2007 | Lee et al. | 435/69.1 |
| 7,384,775 B2 | 6/2008 | Zagursky et al. | |
| 7,635,487 B2 | 12/2009 | Meinke et al. | |
| 2005/0020813 A1 | 1/2005 | Masignani et al. | |
| 2006/0264378 A1 | 11/2006 | Fujii et al. | |
| 2008/0085277 A1 | 4/2008 | Cho et al. | |
| 2011/0130300 A1 | 6/2011 | Ochs-Onolemhemhen et al. | |

FOREIGN PATENT DOCUMENTS

| | | |
|---|---|---|
| WO | WO 00/06737 | 2/2000 |
| WO | 02/077021 | * 10/2002 |
| WO | WO 02/077021 | 10/2002 |
| WO | WO 02/083855 | 10/2002 |
| WO | WO 2004/092209 | 10/2004 |

OTHER PUBLICATIONS

Amsbaugh, et al., "Genetic Control of the Antibody Response to Type III Pneumococcal Polysaccharide in Mice" *J. Exp. Med.* 136:931-949 (1972).

Avery, et al., "Studies on the Chemical Nature of the Substance Inducing Transformation of Pneumococcal Types" *J. Exp. Med.* 149:297-326 (1979).

Balachandran, et al., "Role of Pneumococcal Surface Protein C in Nashopharyngeal Carriage and Pneumonia and Its Ability to Elicit Protection against Carriage of *Streptococcus pneumoniae*" *Infection and Immunity* 70:2526-2534 (2002).

Berry, et al., "Cloning and expression of the pneumococcal neuraminidase gene in *Escherichia coli*" *Gene* 71:299-305 (1988).

Berry, et al., "Cloning and Characterization of nanB, a Second *Streptococcus pneumoniae* Neuraminidase Gene, and Purification of the NanB Enzyme from Recombinant *Escherichia coli*" *Journal of Bacteriology* 178(16):4854-4860 (1996).

(Continued)

*Primary Examiner* — Albert Navarro
(74) *Attorney, Agent, or Firm* — Kilpatrick Townsend & Stockton LLP

(57) ABSTRACT

Provided herein are compositions designed to reduce or prevent bacterial infections (for example pneuomococcal infections), nasal carriage, nasal colonization, and central nervous system invasion. Provided herein is a composition comprising a pneumococcal neuraminidase, phosphocholine, pneumococcal teichoic acid, pneumococcal lipoteichoic acid, or an antigenic portion of either neuraminidase, phosphocholine, pneumococcal teichoic acid, pneumococcal lipoteichoic acid. Optionally, the composition can comprise any combination of a pneumococcal neuraminidase, a phosphocholine, a pneumococcal teichoic acid, a pneumococcal lipoteichoic acid or an antigenic portion of any one of these. Optionally the agents are detoxified. Further provided are methods of making and using the compositions disclosed herein. Specifically provided are methods of generating antibodies in a subject comprising administering to the subject an agent or composition taught herein. Also provided are methods of reducing or preventing nasal carriage or pneumococcal infection in a subject comprising administering to the subject a composition taught herein.

12 Claims, 17 Drawing Sheets

(56) References Cited

OTHER PUBLICATIONS

Berry, et al., "Additive Attenuation of Virulence of *Streptococcus pneumoniae* by Mutation of the Genes Encoding Pneumolysin and Other Putative Pneumococcal Virulence Proteins" *Infection and Immunity* 68:133-140 (2000).

Black, et al., "Efficacy, safety and immunogenicity of heptavalent pneumococcal conjugate vaccine in children. Northern California Kaiser Permanente Vaccine Study Center Group" *Pediatr. Infect. Dis. J.* 19:187-195 (2000).

Briles, et al., "Mouse Igg3 antibodies are highly protective against infection with *Streptococcus pneumoniae*" *Nature* 294(5836):88-90 (1981).

Briles, et al., "Antiphosphocholone Antibodies Found in Normal Mouse Serum are Protective Against Intravenous Infection with Type 3 *Streptococcus Pneumoniae*" *J Exp. Med.* 153:694-705 (1981).

Briles, et al., "The effects of idiotype on the ability of IgG1 anti-phosphorylcholine antibodies to protect mice from fatal infection with *Streptococcus pneumoniae*" *Eur. J. Immunol.* 14:1027-1030 (1984).

Briles, et al., "The effects of subclass on the ability of anti-phosphocholine antibodies to protect mice from fatal infection with *Streptococcus pneumoniae*" *J Mol. Cell. Immunol.* 1:305-309 (1984).

Briles, et al., "Genetic control of the susceptibility to pneumococcal infection." *Curr. Top. Microbiol. Immunol.* 124:103-120 (1986).

Briles, et al., "Antipneumococcal Effects of C-Reactive Protein and Monoclonal Antibodies to Penumococcal Cell Wall and Capsular Antigens" *Infection and Immunity* 57(5):1457-1464 (1989).

Briles, et al., "Strong Association between Capsular Type and Virulence for mice among Human Isolates of *Streptococcus pneumoniae*" *Infection and Immunity* 60:111-116 (1992).

Briles, et al., "Immunizations with Pneumococcal Surface Protein a and Pneumolysin are Protective against Pneumonia in a Murine Model of Pulmonary Infection with *Streptococcus pneumoniae*" *J. Infect. Dis.* 188:339-348 (2003).

Briles, et al., "Nasal Colonization with *Streptococcus pneumoniae* Includes Subpopulations of Surface and Invasive Pneumococci" *Infection and Immunity* 73(10):6945-6951 (2005).

Brooks-Walter, et al., "The pspC gene of *Streptococcus pneumoniae* encodes a polymorphic protein, PspC, which elicits cross-reactive antibodies to PspA and provides immunity to pneumococcal bacteremia" *Infection and Immunity* 67:6533-6542 (1999).

Camara, et al., "A neuraminidase from *Streptococcus pneumoniae* has the features of a surface protein" *Infection and Immunity* 62(9):3688-3695 (1994).

Crennell, et al., "Crystal structure of a bacterial sialidase (from *Salmonella typhimurium* LT2) shows the same fold as an influenza virus neuraminidase" *PNAS* 90(21):9852-9856 (1993).

Hoskins, et al., "Genome of the bacterium *Streptococcus pneumoniae* strain R6" *Journal of Bacteriology* 183(19):5709-5717 (2001).

Jedrzejas, "Pneumococcal virulence factors: structure and function" *Microbiol. Mol. Biol. Rev.* 65(2):187-207 (2001).

Kelly, et al., "Neuraminidase activities of clinical isolates of *Diplococcus pneumoniae*" *J. Bacteria* 94:272-273 (1967).

King, et al., "Phase variable desialylation of host proteins that bind to *Streptococcus pneumoniae* in vivo and protect the airway" *Mol. Microbiol.* 54:159-171 (2004).

LaMarco, et al., "Experimental alteration of chinchilla middle ear mucosae by bacterial neuraminidase" *Ann. Otol. Rhinol. Laryngol.* 95:304-308 (1986).

Lock, et al., "Purification and immunological characterization of neuraminidase produced by *Streptococcus pneumoniae*" *Microb. Pathog.* 4:33-43 (1988).

Lock, et al., "Comparative efficacy of pneumococcal neuraminidase and pneumolysin as immunogens protective against *Streptococcus pneumoniae*" *Microb. Pathog.* 5(6):461-467 (1988).

Long, et al., "Immunization with native or recombinant *Streptococcus pneumoniae* neuraminidase affords protection in the chinchilla otitis media model" *Infection and Immunity* 72:4309-4313 (2004).

Madhi and Klugman, "A role for *Streptococcus pneumoniae* in virus-associated pneumonia" *Nat. Med.* 10:811-813 (2004).

Magee and Yother, "Requirement for capsule in colonization by *Streptococcus pneumoniae*" *Infection and Immunity* 69:3755-3761 (2001).

Martinot, et al., "Haemolytic-Uraemic syndrome associated with *Streptococcus pneumoniae* meningitis" *European Journal of Pediatrics* 148(7):648-649 (1989).

Manco, et al., "Pneumococcal neuraminidases A&B both have essential roles during infection of the respiratory trackt & sepsis" *Infection and Immunity* 74(7):4014-4020 (2006).

McCullers and Bartmess, "Role of neuraminidase in lethal synergism between influenza virus and *Streptococcus pnesumoniae*" *J. Infect. Dis.* 187:1000-1009 (2003).

McDaniel, et al., "A protective monoclonal antibody that reacts with a novel antigen of pneumococcal teichoic acid" *Microb. Pathog.* 3:249-260 (1987).

O'Toole, et al., "Neuraminidase activity in bacterial meningitis" *J. Clin. Invest.* 50:979-985 (1971).

Paton, et al., "Molecular analysis of the pathogenicity of *Streptococcus pneumoniae*: the role of pneumococcal proteins" *Annu. Rev. Microbiol.* 47:89-115 (1993).

Paton, et al., "Molecular analysis of putative pneumococcal virulence proteins" *Microb. Drug Resist.* 3(1):1-10 (1997).

Scanlon, et al., "Purification and properties of *Streptococcus pneumoniae* neuraminidase" *Enzyme* 41(3):143-150 (1989).

Shakhnovich, et al., "Neuraminidase expressed by *Streptococcus pneumoniae* desialylates the lipopolysaccharide of *Neisseria meningitidis* and *Haemophilus influenzae*: a paradigm for interbacterial competition among pathogens of the human respiratory tract" *Infection and Immunity* 70:7161-7164 (2002).

Tettelin, et al., "Nasal lymphoid tissue (NALT) as a mucosal immune inductive site" *Science* 293:498-506 (2001).

Tong, et al., "Comparison of structural changes of cell surface carbohydrates in the eustachian tube epithelium of chinchillas infected with a *Streptococcus pneumoniae* neuraminidase-deficient mutant or its isogenic parent strain" *Microb. Pathog.* 31:309-317 (2001).

Tong, et al., "Evaluation of the virulence of a *Streptococcus pneumoniae* neuraminidase-deficient mutant in nasopharyngeal colonization and development of otitis media in the chinchilla model" *Infection and Immunity* 68:921-924 (2000).

Van Ginkel, et al., "Cutting edge: the mucosal adjuvant cholera toxin redirects vaccine proteins into olfactory tissues" *J. Immunol.* 165:4778-4782 (2000).

Van Ginkel, et al., "Pneumococcal carriage results in ganglioside-mediated olfactory tissue infection" *PNAS* 100(24):14363-14367 (2003).

Wu, et al., "Nasal lymphoid tissue (NALT) as a mucosal immune inductive site" *Scand. J. Immunol.* 46:506-513 (1997).

Wu, et al., "Establishment of a *Streptococcus pneumoniae* nasopharyngeal colonization model in adult mice" *Microb. Pathog.* 23:127-137 (1997).

Yother, et al., "Protection of mice from infection with *Streptococcus pneumoniae* by anti-phosphocholine antibody" *Infection and Immunity* 36:184-188 (1982).

Yother, et al., "Truncated forms of PspA that are secreted from *Streptococcus pneumoniae* and their use in functional studies and cloning of the pspA gene" *J. Bact.* 174:610-618 (1992).

Yother, et al., "Transformation of encapsulated *Streptococcus pneumoniae*" *J. Bact.* 168:1463-1465 (1986).

Sanchez-Beato et al., "Molecular Characterization of PCPA: a novel chlorine-binding protein of *Streptococcus pneumoniae*," *FEMS Micro. Letters* 164:207-214 (1998).

Yesilkaya et al., "Identification of amino acids essential for catalytic activity of pneumococcal neuraminidase A" *Research in Microbiology* 157:569-574 (2006).

AlosonDeValasco et ai., "*Streptococcus pneumoniae*: virulence factors, pathogenesis, and vaccines," *Microbiological Reviews* 59:591-603 (1995).

(56) References Cited

OTHER PUBLICATIONS

Briles et al., "Mouse antibody to phosphocholine can protect mice from infection with mouse-virulent human isolates of *Streptococcus pneumoniae*," Infection and Immunity 60:1957-62 (1992).

Trolle et al., "Intranasal immunization with protein-linked phosphorylcholine protects mice against a lethal intranasal challenge with *Streptococcus pneumoniae*," Vaccine 18:2991-8 (2000).

English Translation of Office Action issued by Korean Patent Office on Feb. 29, 2012 in related Korean Application No. 10-2006-7009031.

Briles et al., "Anti-phosphorylcholine antibodies of the T15 idiotype are optimally protective against *Streptococcus pneumoniae*", J. Exp. Med., vol. 156, Oct. 31, 1982, pp. 1177-1185.

English translation of Office Action from related Israel Application No. 175499, Feb. 20, 2014, 2 pages.

Japanese Office Action and English translation of same from related Japanese Application No. JP2011-113958. Feb. 20, 2014, 11 pages.

Gillespie, "Aspects of pneumococcal infection including bacterial virulence, host response and vaccination" J. Med. Microbiol. vol. 28 (1989), pp. 237-248.

Office action for Chinese Application No. 201210290765.4 mailed Jul. 11, 2014 including an English translation.

Office Action for Chinese Patent Application No. 201210290765.4, mailed on Jan. 6, 2015 including an English translation, 12 pages.

English translation of Office action for Israeli Application No. 175499, Jan. 29, 2015.

\* cited by examiner

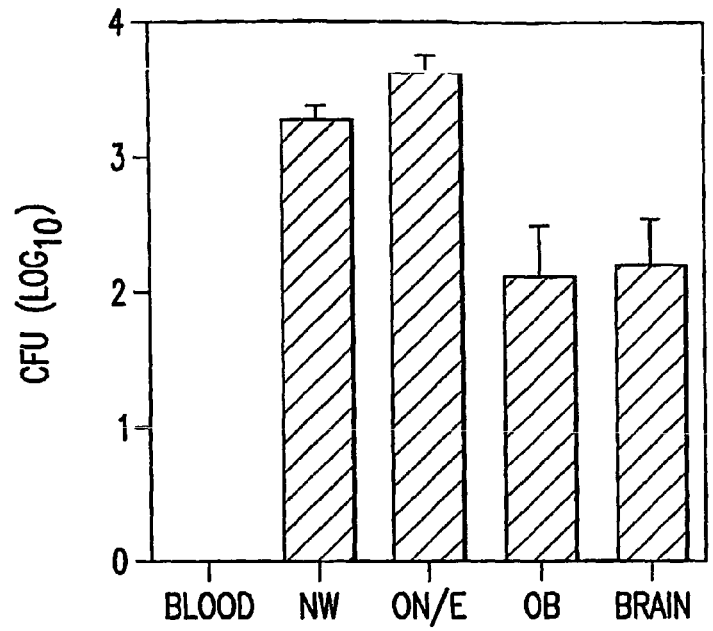
FIG.4A
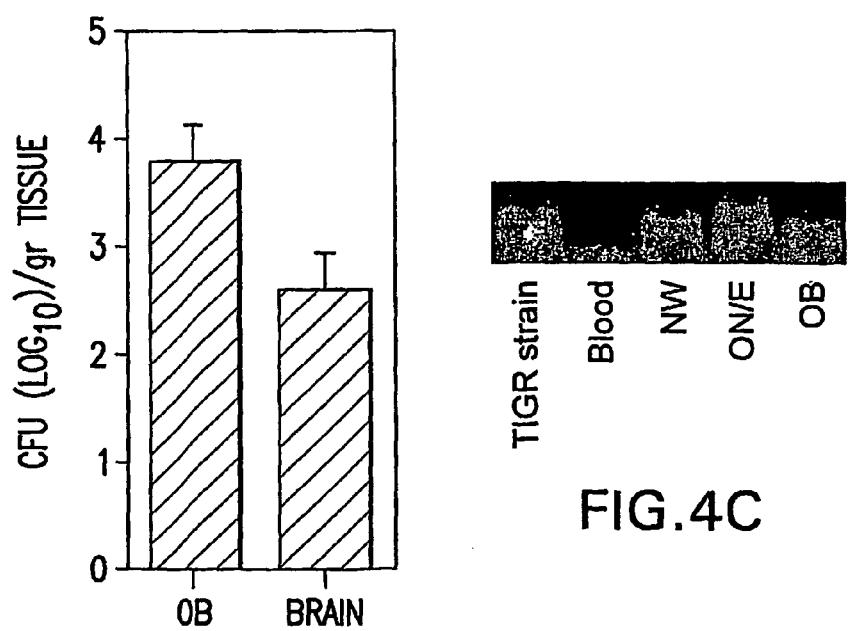
FIG.4B
FIG.4C

COMPOSITIONS FOR REDUCING BACTERIAL CARRIAGE AND CNS INVASION AND METHODS OF USING SAME

CROSS-REFERENCE TO RELATED APPLICATION

This application claims the benefit of U.S. Provisional Application No. 60/518,799, filed on Nov. 10, 2003, which is hereby incorporated herein by reference in its entirety.

ACKNOWLEDGEMENTS

This invention was made with government support under Grants DC 04976, AI 21548, and P30 DK 54781 from the National Institutes of Health and under contract NO1 AI 65299 from the National Institute of Allergy and Infectious Diseases. The government has certain rights in the invention.

BACKGROUND

*Streptococcus pneumoniae* is a rather ubiquitous human pathogen, which can infect several organs including lungs, the central nervous system (CNS), the middle ear, and the nasal tract. Infection of these tissues results in various symptoms such as bronchitis, pneumonia, meningitis, and sinus infection. *S. pneumoniae* is a major cause of bacterial meningitis in humans and is associated with significant mortality and morbidity despite antibiotic treatment. Quagliarello et al., (1992) N. Eng. J. Med. 327: 869-872. *S. pneumoniae* meningitis can cause persistent neurological sequelae. The incidence of *S. pneumoniae* meningitis in developed versus developing countries are 1-2 and 20 per 100,000 population, respectively. Anon, (2000) CDSC European Bacterial Meningitis Surveillance Project. The fatality rate of pneumococcal meningitis in the USA is approximately 18%. Fedson et al., (1994) Arch. Intern. Med. 154:2531-2535. The highest incidence of pneumococcal meningitis occurs in children between 1-4 years of age (30% of all bacterial meningitis), followed by 15-19 year olds (14%) and 1-11 month old infants (13%). Anon, (2000) CDSC European Bacterial Meningitis Surveillance Project. The elderly are also seriously affected by streptococcal meningitis in both developed and developing countries. Butler et al., (1999) Drugs Aging 15 (Suppl. 1): 11-19; Fedson et al., (1999) Vaccine 17 Suppl. 1: S11-18.

The major reservoir of pneumococci in the world resides in human nasal carriage. Acquisition of infection is generally from a carrier and infection is always preceded by nasal carriage. The colonization of the nasopharynx is considered a prerequisite for the spread of pneumococci to the lower respiratory tract, the nasal sinuses, and the middle ear. Thus, any medical intervention that prevented carriage would not only eliminate the risk of disease in the treated individuals but would also result in herd immunity and greatly lower the risk of infection even in untreated members of the community. Although *S. pneumoniae* is an important human pathogen, relative little is known about the mechanisms by which *S. pneumoniae* causes either nasal carriage or meningitis.

Some data exist to suggest that neuraminidases are unique virulence factors for the nasal tract. One such observation comes from the study of the NanA-deficient, *S. pneumoniae* strain D39, which is eliminated faster from the nasopharynx than is its parent strain. Tong et al., (2002) Infect. Immun. 68: 921-924. Neuraminidase cleaves terminal sialic acid residues from a wide variety of glycolipids, glycoproteins, and oligosaccharides on the host cell surfaces and in body fluids. Elevated levels of free sialic acid in the cerebrospinal fluid (CSF) of patients with pneumococcal meningitis are associated with a poor prognosis. O'Toole et al., (1971) J. Clin. Invest. 50: 979-985. The importance of this enzyme for *S. pneumoniae* virulence in humans is further illustrated by the findings of two independent studies where every new clinical isolate of *S. pneumoniae* had neuraminidase activity. O'Toole et al., (1971) J. Clin. Invest. 50: 979-985; Kelly et al., J. Bacteriol. 94: 272-273. Moreover, mouse passage of isolates of pneumococci, which frequently increases their virulence, has been reported to also result in 2-5-fold increase of neuraminidase activity. Vishniakova et al., (1992) Zhurnal Mikrobiologii, Epidemiologii i Immunobiologii 9-10: 26-9. Pneumococcal C-polysaccharide, also known as teichoic acid, is structurally identical to the polysaccharide portion of pneumococcal F-antigen, also known as lipoteichoic acid. Fischer et al., (1993) Eur. J. Biochem 215: 851-857. These molecules are unique features of *S. pneumoniae* among gram-positive bacteria. The immunodominant determinants on these molecules are the phosphorylcholine (PC) residues and Abs to PC are protective against intraperitoneal, intravenous, or nasal pneumococcal challenge. Briles et al., (1984) Eur. J. Immunol. 14: 1027-1030; Briles et al., (1981) Nature 294: 88-90; Yother et al., (1982) Infect. Immun. 36: 184-188; Briles et al., (1984) J. Mol. Cell. Immunol. 1:305-309. However, as all of these studies assessed protection against systemic infection medicated by serum, no information is available regarding the ability of these Abs to protect against nasal colonization. Surface phosphocholine residues are, however, common on the surface of respiratory bacteria. Lysenko, et al., (2000) Infect. Immun. 68:1664-71.

The mechanisms by which *S. pneumonia* causes nasal carriage and subsequent disease are relatively unknown. No studies to date have determined a mechanism by which nasal carriage is reduced or prevented. Since colonization of the nasopharynx is considered a prerequisite for the spread of pneumnococci to the lower respiratory tract, the nasal sinus, systemically, and to the brain, what is needed in the art is a means of providing mucosal immunity at the site of initial pneumococcal colonization. Preventing initial pneumococcal colonization in the nasopharynx, will prevent nasal carriage and reduce spread of *S. pneumoniae* between individuals. Moreover, providing immunity at the mucosal surfaces of the nasopharynx would prevent or reduce subsequent disease caused by *S. pneumoniae*.

SUMMARY OF THE INVENTION

Provided herein are compositions designed to reduce or prevent bacterial infections (for example pneumococcal infections), nasal carriage, nasal colonization, and CNS invasion. Optionally, the compositions are designed for mucosal administration. Provided herein are detoxified pneumococcal neuramidase, phosphocholine, pneumococcal teichoic acid, pneumococcal lipoteichoic acid, or an antigenic portion of any one of these and compositions comprising these detoxified agents.

Also provided are compositions comprising a pneumococcal neuraminidase, phosphocholine, pneumococcal teichoic acid, pneumococcal lipoteichoic acid, or an antigenic portion of any one of these and a pharmaceutically acceptable carrier. Optionally, the composition can comprise any combination of a pneumococcal neuraminidase, a phosphocholine, a pneumococcal teichoic acid, a pneumococcal lipoteichoic acid or an antigenic portion of any one of these. Also provided are detoxified pneumococcal neuraminidase, phosphocholine, pneumococcal teichoic acid, pneumococcal lipoteichoic acid, or an antigenic portion of any one of these as well as compositions containing the detoxified agents and methods of using the agents.

Also provided are methods of generating in a subject antibodies to pneumococcal neuraminidase, phosphocholine, pneumococcal teichoic acid, pneumococcal lipoteichoic acid, or an antigenic portion of any one of pneumococcal neuraminidase, phosphocholine, pneumococcal teichoic acid, or pneumococcal lipoteichoic acid comprising administering to the subject a composition comprising the agents. Optionally, the composition is suitable for administration to a mucosal surface or for systemic administration.

Further provided is a composition comprising antibodies to a pneumococcal neuraminidase, phosphocholine, pneumococcal teichoic acid, pneumococcal lipoteichoic acid, or an antigenic portion of any one of these, along with a pharmaceutically acceptable carrier. Optionally the composition is suitable for administration to a mucosal surface or for systemic administration.

Further provided are methods of reducing or preventing nasal carriage, nasal colonization, or bacterial infection (for example pneumococcal infection) in a subject comprising contacting the nasal mucosa of the subject with a composition taught herein.

Additional advantages will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 4 shows detection of the TIGR4 strain of *S. pneumoniae* in the OBs following nasal challenge. An aliquot of $5\times10^5$ CFU was given nasally and the blood, NWs, ON/E, OBs and brain tissues were analyzed for colonization one week after challenge (panels A and B). These tissues (10 µg DNA) were also analyzed for the presence of the pneumolysin gene by PCR (panel C). In addition, the *S. pneumoniae* were visualized by immunofluorescence with PspA-specific Abs in the OBs of control (I) or *S. pneumoniae* challenged mice (panels E and F). Indicated are the mean+one SE. The data are representative of three separate experiments.

DETAILED DESCRIPTION

Figure 1:
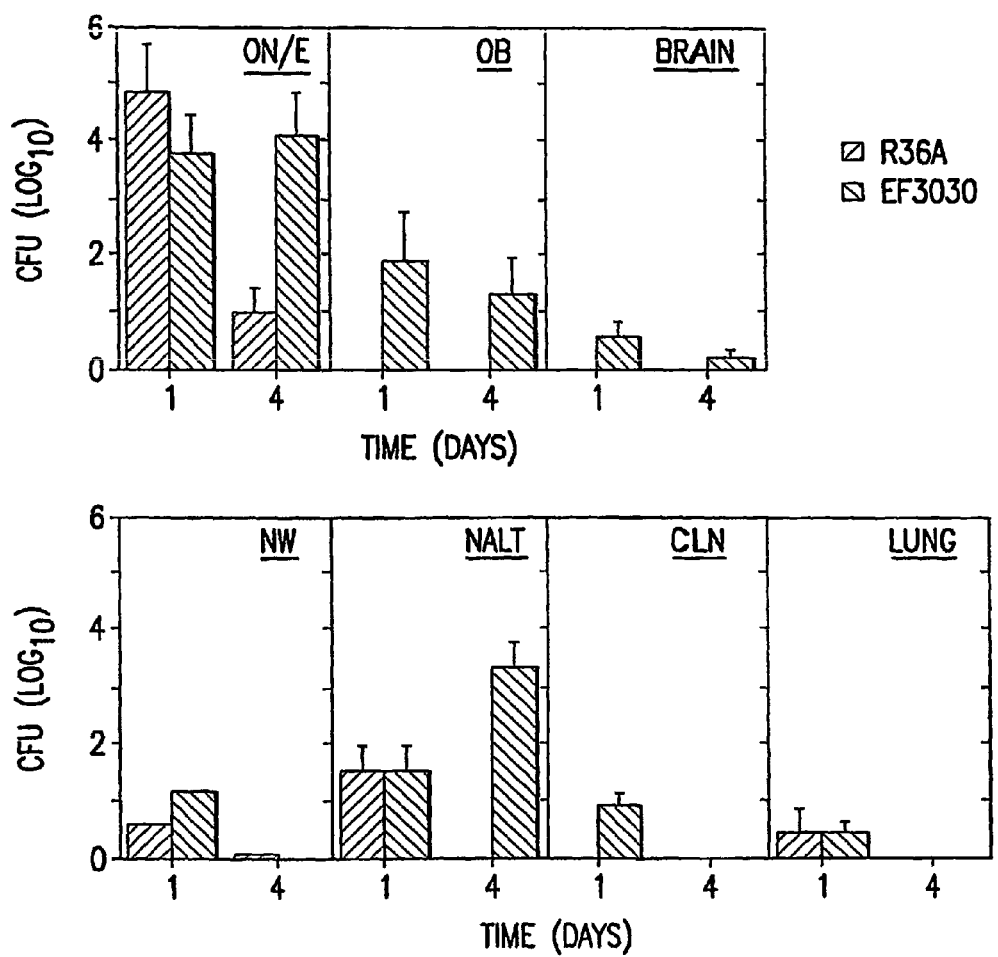
FIG. 1 shows nasal delivery of $3\times10^6$ CFU of either the nonencapsulated R36A strain or the virulent EF3030 strain of *S. pneumoniae* to xid mice. The neuronal tissues ON/E, OBs, brain and the lymphoid tissues (NALT, CLN and lungs) were collected, minced and analyzed for the presence of live pneumococci at 1 and 4 days after nasal challenge. Indicated is the mean of $\log_{10}$ colony forming units (CFUs)+one standard error (SE). The 0 value on the Y-axis represents the absence of detectable CFUs. Indicated are the mean CFUs+SE of 5 mice per group and are representative of three different experiments.

Before the present compounds, compositions, articles, devices, and/or methods are disclosed and described, it is to be understood that the aspects described below are not limited to specific synthetic methods or specific administration methods, as such may, of course, vary. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise. Thus, for example, reference to "an antigenic fragment" includes mixtures of antigenic fragments, reference to "a pharmaceutical carrier" or "adjuvant" includes mixtures of two or more such carriers or adjuvants, and the like.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human.

"Optional" or "optionally" means that the subsequently described event or circumstance can or cannot occur, and that the description includes instances where the event or circumstance occurs and instances where it does not. For example, the phrase "optionally the composition can comprise a combination" means that the composition may comprise a combination of different molecules or may not include a combination such that the description includes both the combination and the absence of the combination (i.e., individual members of the combination).

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Provided herein are compositions and methods designed to reduce or prevent bacterial infections (for example pneumococcal infections), nasal carriage, nasal colonization, and CNS invasion. *S. pneumoniae* colonizes the nasal tract in part by crossing the epithelial barrier through C-polysaccharide-ganglioside interactions with subsequent endocytosis into epithelial cells. C-polysaccharide binds to asialo-GM1, asialo-GM2, and fucosyl-asialo-GM1 through binding to a terminal or internal GalNAcβ1-4Gal sequence in the ganglioside. Although the abundancy of these asialogangliosides in the plasma membrane of cells is normally low, with the exception of the human lungs *S. pneumoniae* has two neuraminidases, NanA and NanB (Berry et al., (1996) J. Bacteriol. 178: 4854-4860), which can each cleave α2,3- and α2,6-linkages of N-acetylneuraminic acid to galactose, and α2,6-linkage to N-acetyl-galactosamine. Scanlon et al., (1989) Enzyme 41: 143-150. Sialic acid residues on gangliosides are α2,3 linked to galactose. Neuraminidases of *S. pneumoniae* remove end-terminal sialic acid residues, which are present on all monosialogangliosides, and galactose-linked multiple sialic acid residues, as seen in the di- and trisialogangliosides. Thus, they should be able to expose the GalNAcβ1-4Gal sequence found in the most common mammalian cell surface gangliosides. These residues are the presumed C-polysaccharide binding site on the cell surface. Using its NanA, which is normally more cell wall associated, and NanB, which is thought to be secreted, *S. pneumoniae* generates its own attachment sites on epithelial cells in the respiratory tract. Thus, pneumococcal C-polysaccharide binds to asialogangliosides, in particular asialo-GM1, and the neuraminidases, which can convert the rather abundant GM1 into asialo-GM1, may create abundant binding sites on ON/E for the C-polysaccharide. This mechanism facilitates nasal carriage and provides access for *S. pneumoniae* to the CNS through the nasal olfactory nerves and epithelium covering the nasal turbinates (ON/E), olfactory bulbs (OB). Similarly, otitis media and other infections involving *S. pneumoniae* can similarly gain access to the CNS through nerves innervating the middle ear. Other bacteria in addition to *S. pneumoniae* have comparable neuraminidases, thus the same mechanism occurs in other bacteria as well. Thus disclosed herein are compositions and methods targeting this mechanism in a variety of bacteria. The agents, compositions, and methods taught herein are directed to interrupting this mechanism to reduce carriage and to prevent CNS invasion.

Optionally, the compositions are designed for mucosal administration. For example, provided herein is a composition comprising a pneumococcal neuraminidase, a phosphocholine, a pneumococcal teichoic acid, a pneumococcal lipoteichoic acid or an antigenic portion of any one of these and a pharmaceutically acceptable carrier, wherein the composition is suitable for administration to a mucosal surface. Optionally, the composition can comprise any combination of a pneumococcal neuraminidase, a phosphocholine, a pneumococcal teichoic acid, a pneumococcal lipoteichoic acid or an antigenic portion of any one of these.

Optionally, the composition is in the form of an aerosol, nasal mist, nasal spray, nasal drops, a nebulizer solution, an aerosol inhalant, a suppository, or any form appropriate for mucosal administration (including oral administration). Optionally, the compositions can be in microspheres or in liposomes for delivery. By "administration to a mucosal surface" is meant administration to any mucosal surface including the respiratory system, the gastrointestinal system, or the urogenital system. Examples of mucosal surfaces include but are not limited to the nasal cavity (including to the olfactory neuroepithelium), the nasopharynx, the rectum, the vagina, the larynx, the mouth, the Eustachian tube, the trachea, the bronchi and other airways, and the intestinal mucosa.

For administration to a mucosal surface a mucosal adjuvant can be used. The adjuvant can administered concomitantly with the composition of the invention, immediately prior to, or after administration of the composition. Optionally, the composition further comprises the adjuvant. Mucosal adjuvant formulations include, for example, an agent that targets mucosal inductive sites. The adjuvant may optionally be selected from the group including, but not limited to, cytokines, chemokines, growth factors, angiogenic factors, apoptosis inhibitors, and combinations thereof. When a cytokine is chosen as an adjuvant, the cytokine may be selected from the group including, but not limited to, interleukins including IL-1, IL-1γ, IL-1β, IL-2, IL-5, IL-6, IL-12, IL-15 and IL-18; transforming growth factor-beta (TGF-β); granulocyte macrophage colony stimulating factor (GM-CSF); interferon-gamma (FN-γ); or other cytokine which has adjuvant activity. Portions of cytolines, or mutants or mimics of cytolines (or combinations thereof), having adjuvant activity or other biological activity can also be used in the compositions and methods of the present invention.

When a chemokine is chosen as an adjuvant, the chemokine may optionally be selected from a group including, but not limited to, Lymphotactin, RANTES, LARC, PARC, MDC, TARC, SLC and FKN. When an apoptosis inhibitor is chosen as an adjuvant, the apoptosis inhibitor may optionally be selected from the group including, but not limited to, inhibitors of caspase-8, and combinations thereof. When an angiogenic factor is chosen as an adjuvant, the angiogenic factor may optionally be selected from the group including, but not limited to, a basic fibroblast growth factor (FGF), a vascular endothelial growth factor (VEGF), a hyaluronan (HA) fragment, and combinations thereof. Indeed, plus (+) and minus (−) angiogenic factors may be chosen as adjuvants.

Other examples of substantially non-toxic, biologically active mucosal adjuvants of the present invention include hormones, enzymes, growth factors, or biologically active portions thereof. Such hormones, enzymes, growth factors, or biologically active portions thereof can be of human, bovine, porcine, ovine, canine, feline, equine, or avian origin, for example, and can be tumor necrosis factor (TNF), prolactin, epidermal growth factor (EGF), granulocyte colony stimulating factor (GCSF), insulin-like growth factor (IGF-1), somatotropin (growth hormone) or insulin, or any other hormone or growth factor whose receptor is expressed on cells of the immune system.

Adjuvants for mucosal administration also include bacterial toxins, e.g., the cholera toxin (CT), the *E. coli* heat-labile toxin (LT), the *Clostridium difficile* toxin A and the pertussis toxin (PT), or combinations, subunits, toxoids, chimera, or mutants thereof. For example, a purified preparation of native cholera toxin subunit B (CTB) can be used. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as RH3-ligand; CpG-motif oligonucleotide; a bacterial monophosphoryl lipid A (MPLA) of, e.g., *E. coli, Salmonella minnesota, Salmonella typhimurium,* or *Shigella flexneri*; saponins (e.g., QS21), orpolylactide glycolide (PLGA) microspheres, can also be used in mucosal administration. Possible other mucosal adjuvants are defensins and CpG motifs containing oligonucleotides.

As used throughout, a "pharmaceutically acceptable carrier" is meant as a material that is not biologically or otherwise undesirable, i.e., the material can be administered to an individual along with the selected compound without causing any undesirable biological effects or interacting in a deleterious manner with any of the other components of the pharmaceutical composition in which it is contained.

Any of the compositions described herein can be used therapeutically with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E. W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically would be standard carriers for administration of compositions to humans in one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

By a pneumococcal neuraminidase is meant any neuraminidase molecule found in pneumococcal bacteria Table 1 shows the alignment of neuraminidases from several species. Neuraminidase molecules also include, for example, SP1326. The SP1326 amino acid sequence can be accessed via GenBank Acession No. AAK75424. Tettelin, H., et al., (2001) Science 293: 498-506. All of the information, including any amino acid and nucleic acid sequences provided for SP1326 under GenBank Accession No. AAK75424 is hereby incorporated in its entirety by this reference. As identified throughout, the amino acid residues for all amino acid sequences are numbered in accordance with the amino acid sequence of pneumococcal strain R6 as shown in Table 1.

TABLE 1

ClustalW (v1.4) multiple sequence alignment

| | |
|---|---|
| 3 Sequences Aligned | Alignment Score = 6332 |
| Gaps Inserted = 32 | Conserved Identities = 105 |
| Pairwise Alignment Mode: Slow | |
| Pairwise Alignment Parameters: | |
| Open Gap Penalty = 10.0 | Extend Gap Penalty = 0.1 |
| Similarity Matrix: blosum | |
| Multiple Alignment Parameters: | |
| Open Gap Penalty = 10.0 | Extend Gap Penalty = 0.1 |
| Delay Divergent = 40% | Gap Distance = 8 |

TABLE 1-continued

ClustalW (v1.4) multiple sequence alignment

```
Similarity Matrix: blosum
Processing time: 3.5 seconds
R6 NanA          1 MSYFRNRDIDIERNSMNRSVQERKCRYSIRKLSVGAVSMIVGAVVFGTSP     50
TIGR4 NanA       1               MNRSVQERKCRYSIRKLSVGAVSMIVGAVVNGTSP     35
S. typhimirium   1                                                        0

R6 NanA         51 VLAQEGASEQPLANETQLSGESSTLTDTEKSQPSSETELSGNKQEQERKD    100
TIGR4 NanA      36 VLAQEGASEQPLANETQLSGESSTLTDTEKSQPSSETELSGNKQEQERKD     85
S. typhimirium   1                                                        0

R6 NanA        101 KQEEKIPRDYYARDLENVETVIEKEDVETNASNGQRVDLSSELDKLKKLE    150
TIGR4 NanA      86 KQEEKIPEDYYARDLENVETVIEKEDVETNASNGQRVDLSSELDKLKKLE    135
S. typhimirium   1                                                        0

R6 NanA        151 NATVHMEFKPDAKAPAFYNLFSVSSATKKDEYFTMAVYNNTATLEGRGSD    200
TIGR4 NanA     136 NATVHMENKPDAKAPAFYNLNSVSSATKKDEYFTMAVYNNTATLEGRGSD    185
S. typhimirium   1                                                        0

R6 NanA        201 GKQFYNNYNDAPLKVKPGQWNSVTFTVEKPTAELPKGRVRLYVNGVLSRT    250
TIGR4 NanA     186 GKQNYNNYNDAPLKVKPGQWNSVTFTVEKPTAELPKGRVRLYVNGVLSRT    235
S. typhimirium   1                   MTVEKSVVFKAEG----------EHF     16
                                      ****           *          .

R6 NanA        251 SLRSGNFIKDMPDVTHVQIGATKRANNTVWGSNLQIRNLTVYNRALTPEE    300
TIGR4 NanA     236 SLRSGNFIKDMPDVTHVQIGATKRANNTVWGSNLQIRNLTVYNRALTPEE    285
S. typhimirium  17 TDQKG--------------------NTIVGS------------------     27
                    . *                       **. **

R6 NanA        301 VQKRSQLFKRSDLEKKLPEGAALTEKTDIFESGRNGKPNKDGIKSYRIPA    350
TIGR4 NanA     286 VQKRSQLNKRSDLEKKLPEGAALTEKTDIFESGRNGNPNKDGIKSYRIPA    335
S. typhimirium  28 --------------------------------GSGG-----TTKYFRIPA     40
                                                    * .*      * .****

R6 NanA        351 LLKTDKGTLIAGADERRLHSSDWGDIGMVIRRSEDNGKTWGDRVTITNLR    400
TIGR4 NanA     336 LLKTDKGTLIAGADERRLHSSDWGDIGMVIRRSEDNGKTWGDRVTITNLR    385
S. typhimirium  41 MCTTSKGTIVVFADARHNTASDQSFIDTAAARSTDGGKTWNKKIAIYNDR     90
                    . * ***.. ** *. .**  *     ** *.****. .. .* .* .*

R6 NanA        401 DNPKASDPSIGSPVNIDMVLVQDPETKRIFSIYDMFPEGKGIFGMSSQKE    450
TIGR4 NanA     386 DNPKASDPSIGSPVNIDMVLVQDPETKRINSIYDMFPEGKGINGMSSQKE    435
S. typhimirium  91 VNSKLSR-------------VMDP--------------------------    101
                    * * *              * **

R6 NanA        451 EAYKKIDGKTYQILYREGEKGAYTIRENGTVYTPDGKATDYRVVVDPVKP    500
TIGR4 NanA     436 EAYKKIDGKTYQILYREGEKGAYTIRENGTVYTPDGKATDYRVVVDPVKP    485
S. typhimirium 102 ---------TCIVANIQG-------RE--TILVMVGKWNNN----DKTWG    129
                            .  .*      **  *.   **     *

R6 NanA        501 AYSDKGDLYKGNQLLGNIYFTTNKTSPFRIAKDSYLWMSYSDDDGKTWSA    550
TIGR4 NanA     486 AYSDKGDLYKGDQLLGNIYFTTNKTSPNRIAKDSYLWMSYSDDDGKTWSA    535
S. typhimirium 130 AYRDK--------------------AP---DTDWDLVLYKSTDDGVTFSK    156
                   ** **                     .*   *   * *  .  * *** * *

R6 NanA        551 PQDITPMVKADWMKFLGVGPGTGIVLRNGPHKGRILIPVYTTNNVSHLNG    600
TIGR4 NanA     536 PQDITPMVKADWMKFLGVGPGTGIVLRNGPHKGRILIPVYTTNNVSHLDG    585
S. typhimirium 157 VETNIHDIVTKNGTISAMLGGVGSGLQLN--DGKLVFPVQMVR-TKNITT    203
                    .   . .      *  *. .   *... **          . .

R6 NanA        601 SQSSRIIYSDDHGKTWHAGEAVNDNRQVDGQKIHSSTMNNRRAQNTESTV    650
TIGR4 NanA     586 SQSSRVIYSDDHGKTWHAGEAVNDNRQVDGQKIHSSTMNNRRAQNTESTV    635
S. typhimirium 204 VLNTSFIYSTD-GITWSLPSGYCEGFGSE---------NN---------I    234
                        *** * **   ..        ..      **        .

R6 NanA        651 VQLNNGDVKLFMRGLTGDLQVATSKDGGVTWEKDIKRYPQVKDVYVQMSA    700
TIGR4 NanA     636 VQLNNGDVKLNMRGLTGDLQVATSKDGGVTWEKDIKRYPQVKDVYVQMSA    685
S. typhimirium 235 IEFN-ASLVNNIR-NSGLRRSFETKDFGKTWTEFPPMDKKVDNR------    276
                    .. *    .*  .*   .* ** ** *               .*

R6 NanA        701 IHTMHEGKEYIILSNAGGPKRENGMVHLARVEENGELTWLKHNPIQKGEF    750
TIGR4 NanA     686 IHTMHEGKEYIILSNAGGPKRENGMVHLARVEENGELTWLKHNPIQKGEN    735
S. typhimirium 277 ----NHGVQGSTITIPSG----NKLVAAHSSAQNKNNDYTRSDISLYAHN    318
                        . *   .. *       *   *.*        .*

R6 NanA        751 AYNSLQELGNGEYGILYEHTEKGQNAYTLSFRKFNWDFLSKDLISPTEAK    800
TIGR4 NanA     736 AYNSLQELGNGEYGILYEHTEKGQNAYTLSNRKNNWENLSKNLISPTEAN    785
S. typhimirium 319 LYSGEVKLIDDFYPKVGNAS--GAGYSCLSYRKN---VDKETLYVVYEAN    363
                     *     *    *   . .*   .*    .** **          *  **
```

TABLE 1-continued

```
ClustalW (v1.4) multiple sequence alignment

R6 NanA        801 VKRTREMGKGVIGLEFDSEVLVNKAPTLQLANGKTARFMTQYDTKTLLFT         850
TIGR4 NanA     786 NRDGQRR----------------DGQRSYWLGVRLRSIGQQGSNPSIGK         818
S. typhimirium 364 ---------------------------------------------GS         365

R6 NanA        851 VDSEDMGQKVTGLAEGAIESMHNLPVSVAGTKLSNGMNGSEAAVHEVPEY         900
TIGR4 NanA     819 WNNSDNPNPVN---------NQDLVVCSRNGRYRTGNYWYSNRKHRKYAN         859
S. typhimirium 366 IEFQDLSRHLP-------------VIKSYN  (SEQ ID NO: 17)        382
                        *          .                .  .

R6 NanA        901 TGPLGTSGEEPAPTVEKPEYTGPLGTSGEEPAPTVEKPEYTGPLGTAGEE         950
TIGR4 NanA     860 SSCKSSR----CQSSWRSKWNQSSGANSSR----IYR-------GSNWYR         894
S. typhimirium 383                                                           382

R6 NanA        951 AAPTVEKPEFTGGVNGTEPAVHEIAEYKGSDSLVTLTTKEDYTYKAPLAQ         1000
TIGR4 NanA     895 ASCSNNR--RVNGINFACNSYYKKRLYLQSSSCSAGTSNNRK-------Q         935
S. typhimirium 383                                                           382

R6 NanA        1001 QALPETGNKESDLLASLGLTAFFLGLFTLGKKREQ (SEQ ID NO: 15)    1035
TIGR4 NanA      936 GENPPSFTRTN--------SNLPWSVYAREKERTI (SEQ ID NO: 16)     962
S. typhimirium  383                                                           382
```

Any antigenic variant of neuraminidase could also be used in the compositions or methods taught herein. Thus, the naturally occurring neuraminidase can be modified by substitution, deletion, or alteration of amino acid residues in accordance with the methods taught herein. Optionally, such modifications will be designed to detoxify the neuraminidase. By "detoxification" is meant a reduction or elimination in enzymatic activity, while maintaining antigencity or immunogenicity. This is accomplished by substitution, deletion, or alteration of amino acids in the active site of the neuraminidase using site specific mutagenesis. Preferably, such substitutions, deletions, or alterations will be within the Asp boxes (i.e., within amino acid residues 460-480, 530-560, or 600-620). See Crennell et al., PNAS 90:9852-9856, which is incorporated herein by reference in its entirety for the neuraminidase structure taught therein. Such substitutions, deletions, or alterations can also occur within the Asp boxes within amino acid residues 383-387, 467-473, 541-546, or 610-616. Alterations in the Asp boxes can include replacement of aspartic acid with glutamic acid or threonine, for example. Other conservative or non-conservative amino acid replacements can also be used at the aspartic acid residue or any other residue in the Asp boxes to reduce toxicity. Other regions of the neuraminidase are optionally targeted for site specific mutagenesis. For example, modifications within the region corresponding to residues 570-580, including for example conservative and non-conservative amino acid substitutions of valine or glutamine at position 572 are disclosed. Also disclosed are neuraminidases with modifications in the regions corresponding to residues 750-760, and more specifically the tyrosine at position 754. Conservative amino acid substitutions for the tyrosine residue include, for example, serine or threonine. Also provided are neuraminidases with modifications in the regions corresponding to amino acid residues 340-350, 600-610, or 360-370. More specifically, the arginines at positions 347, 605, 366, or 367 can be substituted with lysine or glutamine, or any other conservative or non-conservative amino acids. The various modifications taught herein can be used in combination. Thus, one or more conservative or non-conservative amino acid substitutions are optionally present in the same neuraminidase.

As described above, a detoxified neuraminidase is a neuraminidase that exhibits decreased activity as compared to non-detoxified neuraminidase as measured by the assay of Lock, et al. (Microb. Pathog. 4: 33-43, 1988), which is well-known in the art. Using the Lock assay, NanA activity in lysates, serum, or blood are measured using 2'-(4-methylumbelliferyl)-α-D-N-acetylneuraminic acid as the substrate in a enzyme assay (Lock et al. 1988). Ten microliters of substrate are combined with 10 µL of serum and incubated for 5 minutes at 37° C. The reaction is stopped using 0.5M sodium carbonate. Neuraminidase activity is measured in terms of the amount of 4-methylumbelliferone (MU) released per minute. MU has an excitation wavelength of 366 nM and an emission wavelength of 445 nm. It is preferred that the detoxified neuraminidase retain antigenicity or immunogenicity comparable to that of non-detoxified neuraminidase, such that it may be combined with a pharmaceutically acceptable carrier to form an immunological composition. For purposes of comparison, non-detoxified neuraminidase includes, but is not limited to, R6 NanA as shown in Table 1. In preferred embodiments, detoxified neuraminidase exhibits at least 60%, 70%, 80%, or 90% of the activity of a non-detoxified neuraminidase.

Detoxified neuraminidase includes alterations (i.e., substitutions, modifications, or deletions) in its amino acid sequence as compared to non-detoxified neuraminidase. In preferred embodiments, detoxified neuraminidase includes alteration of approximately 7%, 10%, 15% or 20% of the amino acids found within non-detoxified neuraminidase. Preferred amino acid deletions include the deletion of approximately 5, 10 or 15 amino acids from the N-terminus of non-detoxified neuraminidase. Other preferred embodiments include the deletion of approximately 60, 50, 40, 30, 20, 10 or 5 amino acids of the C-terminus of non-detoxified neuraminidase (for the purposes of this application, the C-terminus begins at amino acid 800 of R6 NanA as shown in Table 1). In yet other preferred embodiments, detoxified neuraminidase includes deletion of 17, 9, 8, 7, 4 or 2 amino acids of the C-terminus of non-detoxified neuraminidase. Certain exemplary preferred deletions are illustrated in Table 1 (i.e., the TIGR4 NanA amino acid sequence). Any of these alterations may be combined with one or more other alterations. It is preferred that such detoxified neuraminidase species exhibit approximately 60%, 70%, 80% or 90% of the activity of non-detoxified neuraminidase.

Other conservative and non-conservative substations in neuramindiase may be used so long as the neuraminidase maintains its antigencity or immunogenicity. These conservative substitutions are such that a naturally occurring amino acid is replaced by one having similar properties. Such conservative and nonconservative substitutions optionally alter the enzymatic function of the polypeptide. For example, conservative substitutions can be made according to Table 2.

TABLE 2

Amino Acid Substitutions

| Original Residue | Exemplary Substitutions |
|---|---|
| Arg | Lys |
| Asn | Gln |
| Asp | Glu |
| Cys | Ser |
| Gln | Asn |
| Glu | Asp |
| Gly | Pro |
| His | Gln |
| Ile | leu; val |
| Leu | ile; val |
| Lys | arg; gln |
| Met | leu; ile |
| Phe | met; leu; tyr |
| Ser | Thr |
| Thr | Ser |
| Trp | Tyr |
| Tyr | trp; phe |
| Val | ile; leu |

It is understood that, where desired, modifications and changes may be made in the nucleic acid encoding the polypeptides of this invention and/or amino acid sequence of the polypeptides of the present invention and still obtain a polypeptide having like or otherwise desirable characteristics (e.g., antigenicity or immunogenicity). Such changes may occur in natural isolates or may be synthetically introduced using site-specific mutagenesis, the procedures, such as missmatch polymerase chain reaction (PCR), are well known in the art. For example, certain amino acids may be substituted for other amino acids in a polypeptide without appreciable loss of functional activity. It is thus contemplated that various changes may be made in the amino acid sequence of the polypeptides of the present invention (or underlying nucleic acid sequence) without appreciable loss of biological utility or activity and possibly with an increase in such utility or activity.

Deletions of the nanA gene or any portion of the nanA gene are carried out using the method described by Sung et al., (2001) Appl Environ Microbiol 67: 5190-5196, which is incorporated herein by reference in its entirety for the methods taught therein. The reagent 2, 3 butadione, which specifically reacts with Arg residues of proteins, is used to assess the importance of Arg residues to the folding of the NanA molecule. Site-directed mutagenesis is used to alter specific amino-acids.

The neuraminidase can also be detoxified by chemical treatment, including for example denaturation. Chemical treatment can also be combined with site-specific mutagenesis to further reduce negative side effects and improving antigenicity or immunogenicity. The detoxified neuraminidase can be treated with an agent such as formalin, glutaraldehyde, heat, or with other agents known to those skilled in the art, prior to immunization of a subject with the detoxified neuraminidase.

Thus provided herein is a detoxified pneumococcal neuraminidase or an antigenic or immunogenic portion thereof. Also provided are compositions comprising the detoxified pneumococcal neuraminidase and a pharmaceutically acceptable carrier. Optionally the composition further comprises an adjuvant (including, for example, a mucosal adjuvant).

Furthermore, moieties can be added to the neuraminidase, including, for example, moieties that increase antigenicity or immunogenicity. Such moieties include, for example, cytokines, chemokines, growth factors, angiogenic factors, apoptosis inhibitors, hormones, toxins, or other moieties discussed herein for use as adjuvants. The moieties can optionally be modified or truncated for use in the altered molecules. Thus provided herein is a pneumococcal neuraminidase chimera comprising the neuraminidase or an antigenic or immunogenic fragment thereof and a moiety that enhances antigenicity or immunogenicity. Also provided are compositions comprising the pneumococcal neuraminidase derivatives and a pharmaceutically acceptable carrier. Optionally the composition further comprises an adjuvant (including, for example, a mucosal adjuvant).

Optionally the modified neuraminidase fragment or portion thereof of the invention has an amino acid sequence with at least about 70% homology with a naturally occurring pneumococcal neuraminidase or fragment thereof. Further provided are nucleic acids that encode the modified neuraminidases or fragments thereof. It is understood that one way to define any known variants and derivatives or those that might arise, of the disclosed nucleic acids and proteins herein is through defining the variants and derivatives in terms of homology to specific known sequences. For example, the amino acid sequence encoded by the nanA gene of the R6 pneumococcal strain as shown in Table 1 sets forth a particular sequence of a pneumococcal neuraminidase and sets forth a particular amino acid sequence of the protein. Specifically disclosed are variants of this sequence herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

By "a pneuomococcal phosphocholine, a pneumococcal teichoic acid, a pneumococcal lipoteichoic acid" is meant a phosphocholine, a teichoic acid, or a lipoteichoic acid present in pneumococcal bacteria. These compounds can be modified, detoxified, or enhanced as described above for the neuraminidase. Provided herein are compositions comprising the modified, detoxified, and enhanced compounds.

By "an antigenic portion thereof" is meant any epitope of a molecule or compound (e.g., neuraminidase, phosphocholine, a pneumococcal teichoic acid, a pneumococcal lipoteichoic acid) that elicits antibody production, wherein the antibody is directed to the molecule. Preferably, the antigenic portion elicits immunity to the molecule or to S. pneumoniae.

Preferably the antibodies are directed to or interfere with active sites of the neuraminidase. Examples of antigenic fragments include, but are not limited to, residues corresponding to residues 63-361 of the nanA-R6 amino acid sequence, in the presence or absence of conservative amino acid substitutions or modifications. Other examples include the Asp regions of neuraminidase (corresponding to residues 460-480, 530-560, 610-620 of the NanA-R6 amino acid sequence) and regions corresponding to 340-350, 360-370, 600-610, 570-580 and 750-760 of the NanA-R6 amino acid sequence, in the presence or absence of conservative amino acid substitutions or modifications. Optionally, the antibodies directed to interfere with active sites of neuraminidase can bind to or prevent binding to arginine residues of NanA located at residue 347, 367 or 605 of SEQ ID NO: 15, or to Asp-boxes of NanA located at residues 383-387, 467-473, 541-546 and 610-616 of SEQ ID NO: 15. Moreover, the antibodies can also bind or prevent binding to valine located at residue 575 of SEQ ID NO: 15 or tyrosine located at residue 752 of SEQ ID NO: 15. The antibody can also bind to or prevent binding to any combination of the above listed residues of SEQ ID NO: 15.

Other examples of NanA fragments include amino acids 1 to 340, 330 to 630, 620 to 800, 700 to 1030 and 330 to 800. Further provided are fragments that are fusions of two or more of these fragments. Fused fragments include, but are not limited to, regions 1 to 340 fused with regions 620-680. Fused fragments are expressed as a recombinant protein. Fragments that encode these fragments are cloned into an expression vector (pET Vectors; Novagen, Inc.) and the protein is purified. Alternatively, fragments are generated as a synthetic polypeptide from a vendor. Fragments are used to immunize animals to generate antibodies and to crystallize in order to assess three-dimensional structures. Further provided are nucleic acids encoding the fragments in the presence or absence of conservative or non-conservative amino acid modifications, or substitutions, as described herein. Also provided are vectors or expression systems comprising the nucleic acids.

Provided herein are compositions comprising isolated antibodies that specifically bind pneumococcal neuraminidase, phosphocholine, teichoic acid, lipoteichoic acid, or an antigenic portion of one or both of these. Also provided is a composition comprising any combination of the antibodies. Such antibodies are useful in developing passive immunity to *S. pneumoniae*. The antibody compositions further comprise a pharmaceutically acceptable carrier. Optionally, the composition is suitable for administration to a mucosal surface, but other routes of administration are disclosed, including systemic administration as described herein.

Also disclosed herein are methods of generating antibodies specific to pneumococcal neuraminidase, phosphocholine, teichoic acid, lipoteichoic acid, or any epitope of pneumococcal neuraminidase, phosphocholine, teichoic acid, or lipoteichoic acid. Optionally, the antibodies are generated in a subject (i.e., in vivo) by contacting the nasal mucosa of the subject with an effective amount of a composition disclosed herein. Also, disclosed is a method of generating antibodies specific to any combination of pneumococcal neuraminidase, phosphocholine, teichoic acid, lipoteichoic acid, or any epitope of pneumococcal neuraminidase, phosphocholine, teichoic acid, or lipoteichoic acid by contacting the nasal mucosa of the subject with an effective amount of a composition comprising a combination of target molecules or antibodies that target the molecules.

Optionally, the agents described herein, whether naturally occurring, detoxified or otherwise modified, can optionally be administered as a nucleic acid, for example, within a vector. Expression of the nucleic acid would then result in contacting the subject with the desired nucleic acid expressed thereby. Thus, for example, if a nucleic acid encoding pneumococcal neuraminidase is administered to a subject in a form that can be expressed within the subject, then the subject is contacted with the neuraminidase.

In the methods described herein which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by gene gun or other delivery methods such as electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., Proc. Natl. Acad. Sci. U.S.A. 85:4486, 1988; Miller et al., Mol. Cell. Biol. 6:2895, 1986). The recombinant retrovirus can then be used to infect and thereby deliver to the infected cells nucleic acid encoding for example pneumococcal neuraminidase or a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naidini et al., Science 272:263-267, 1996), pseudotyped retroviral vectors (Agrawal et al., Exper. Hematol. 24:738-747, 1996). Physical transduction techniques can also be used, such as liposome delivery and receptor-mediated and other endocytosis mechanisms (see, for example, Schwartzenberger et al., Blood 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, Hum. Gene Ther. 8:985-1001, 1997; Alvarez and Curiel, Hum. Gene Ther. 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., Remington: The Science and Practice of Pharmacy (19th ed.) ed. A. R. Gennaro, Mack Publishing Company, Easton, Pa. 1995.

Also disclosed is a method of reducing or preventing pneumococcal nasal carriage in a subject comprising contact of the nasal mucosa of the subject with an effective amount of a composition disclosed herein. Such administration can be useful in generating active or passive immunity to or protection against pneumococcal infection or nasal carriage.

Further provided is a method of reducing or preventing pneumococcal infection in a subject comprising contact of a mucosal surface of the subject with an effective amount of a composition disclosed herein. For example, the method can prevent pneumococcal meningitis, otitis media, pneumonia, or hemolytic uremia. Prevention or reduction can occur by reducing nasal carriage and or preventing CNS invasion, systemic invasion, or invasion of the Eustachian tubes or lower airways.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The dosages or amounts of the compositions described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied. Preferred dosages include for nasal applications of antigen between about 1-1000 μg per immunization or any amount in between, including for example 10-100 μg.

The efficacy of administration of a particular dose of the compounds or compositions according to the methods described herein can be determined by evaluating the particular aspects of the medical history, signs, symptoms, and objective laboratory tests that are known to be useful in evaluating the status of a subject with pneomococcal infection or who is a pneumococcal carrier. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved (e.g., nasal carriage is reduced or eliminated), 2) the progression of the disease, infection, or nasal carriage is shown to be stabilized, slowed, or reversed, or 3) the need for other medications for treating the disease or condition is lessened or obviated, then a particular treatment regimen will be considered efficacious. For example, reducing or preventing nasal carriage in a subject or in a population, avoiding or reducing the occurrence of CNS invasion or other secondary pneumococcal infections would indicate efficacy. Such effects could be determined in a single subject (e.g., by reducing the number of bacteria detected with a traditional swab of the mucosal surface) or in a population (e.g., using epidemiological studies).

The compounds and pharmaceutical compositions described herein can be administered to the subject in a number of ways depending on whether local or systemic treatment is desired, and on the area to be treated. Thus, for example, a compound or pharmaceutical composition described herein can be administered intravenously, subcutaneously, intramuscularly, encapsulated in liposomes or microspheres, as an ophthalmic solution and/or ointment to the surface of the eye, as a nasal spray, as a nebulized solution, or as an aerosol to the nasal cavities or airways. Moreover, a compound or pharmaceutical composition can be administered to a subject vaginally, rectally, intranasally, orally, by inhalation, orally, or by intubation. Optionally, the composition is administered by intravenous, subcutaneous, intramuscular, or intraperitoneal injection. The composition can be prepared in conventional forms, either as liquid solutions or suspensions, solid forms suitable for solution or suspension in liquid, or as emulsions. Optionally, administration is by slow release or sustained release system such that a constant dosage is maintained. See, e.g., U.S. Pat. No. 3,610,795, which is incorporated by reference herein for the methods taught therein.

The compositions taught herein include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and organic esters such as ethyl oleate. Aqueous carriers include water, alcoholic/aqueous solutions, emulsions or suspensions, including saline and buffered media Vehicles include sodium chloride solution, Ringer's dextrose, dextrose and sodium chloride, lactated Ringer's, or fixed oils. Preservatives and other additives can also be present such as, for example, antimicrobials, anti-oxidants, chelating agents, and inert gases and the like.

Formulations for local administration can include ointments, lotions, creams, gels, drops, suppositories, sprays, liquids, aerosols, nebulizer solutions and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

Provided herein are methods of reducing or preventing nasal carriage or pneumococcal infection in a subject comprising administering to a subject an effective amount of a neuraminidase inhibitor. Preferably, the neuraminidase inhibitor inhibits pneumococcal neuraminidase activity without significantly reducing the subject's endogenous neuraminidase. Thus, for example, if the neuraminidase is administered to a human, the inhibitor will preferably inhibit pneumococcal neuraminidase without reducing the human neuraminidase activity, or without reducing human neuraminidase activity such that negative side-effects results in the human. Examples of known neuraminidase inhibitors include DANA, NANA, zanamivir and oseltamivir.

Provided herein is a method of reducing or preventing nasal carriage or pneumococcal infection in a subject comprising administering to a subject an effective amount of a composition comprising antibodies or fragments thereof against pneumococcal neuraminidase, phosphocholine, pneumococcal teichoic acid, pneumococcal lipoteichoic acid, or antibodies against a portion of any one of these. Optionally this administration comprises contacting a mucosal surface of the subject with the composition. Also provided are compositions and containers containing the antibodies.

The term "phosphocholine antibody" as used herein refers to an antibody that preferentially binds to phosphocholine or an antigenic fragment thereof. Antibodies of the invention can also preferentially bind to pneumococcal teichoic acid or pneumococcal lipoteichoic acid or antigenic portions thereof or to a neuraminidase or a fragment thereof.

The term "antibodies" is used herein in a broad sense and includes both polyclonal and monoclonal antibodies. Chimeric antibodies, and hybrid antibodies, with dual or multiple antigen or epitope specificities, and fragments, such as F(ab')2, Fab', Fab, scFv, and the like, including hybrid fragments can also be used in the compositions and methods described herein. Thus, fragments of the antibodies that retain the ability to bind their specific antigens are provided. For example, fragments of antibodies which maintain neuraminidase, phosphocholine, teichoic acid, or lipoteichoic acid binding activity are included within the meaning of the term "antibody fragment." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, N.Y., (1988)).

Conjugates of antibody fragments and antigen binding proteins (single chain antibodies) can be used in the composition of the invention. Such conjugates are described, for example, in U.S. Pat. No. 4,704,692, the contents of which are hereby incorporated by reference. The antibodies can be tested for their desired activity using in vitro assays, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

The antibody fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response. Thus, the compositions comprising antibodies optionally comprise humanized or fully human antibodies. Antibody humanization techniques generally involve the use of recombinant DNA technology to manipulate the DNA sequence encoding one or more polypeptide chains of an antibody molecule. Accordingly, a humanized form of a non human antibody (or a fragment thereof) is a chimeric antibody or antibody chain (or a fragment thereof, such as an Fv, Fab, Fab', or other antigen binding portion of an antibody) which contains a portion of an antigen binding site from a non-human (donor) antibody integrated into the framework of a human (recipient) antibody.

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86 95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551 255 (1993); Jakobovits et al., Nature, 362:255 258 (1993); Bruggermann et al., Year in Immunol., 7:33 (1993)). Specifically, the homozygous deletion of the antibody heavy chain joining region (J(H)) gene in these chimeric and germ line mutant mice results in complete inhibition of endogenous antibody production, and the successful transfer of the human germ line antibody gene array into such germ line mutant mice results in the production of human antibodies upon antigen challenge. Antibodies having the desired activity are selected using Env-CD4-co-receptor complexes as described herein.

To generate a humanized antibody, residues from one or more complementarity determining regions (CDRs) of a recipient (human) antibody molecule are replaced by residues from one or more CDRs of a donor (non human) antibody molecule that is known to have desired antigen binding characteristics (e.g., a certain level of specificity and affinity for the target antigen). In some instances, Fv framework (FR) residues of the human antibody are replaced by corresponding non human residues. Humanized antibodies may also contain residues which are found neither in the recipient antibody nor in the imported CDR or framework sequences. Generally, a humanized antibody has one or more amino acid residues introduced into it from a source which is non human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522 525 (1986), Reichmann et al., Nature, 332:323 327 (1988), and Presta, Curr. Opin. Struct. Biol., 2:593 596 (1992)).

Methods for humanizing non human antibodies are well known in the art. For example, humanized antibodies can be generated according to the methods of Winter and co workers (Jones et al., Nature, 321:522 525 (1986), Riechmann et al., Nature, 332:323 327 (1988), Verhoeyen et al., Science, 239: 1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Administration of the antibodies can be done as disclosed herein. Nucleic acid approaches for antibody delivery also exist. The antibodies and antibody fragments can also be administered to patients or subjects as a nucleic acid preparation (e.g., DNA or RNA) that encodes the antibody or antibody fragment, such that the subject's own cells take up the nucleic acid and produce and secrete the encoded antibody or antibody fragment. The delivery of the nucleic acid can be by any means known in the art.

Also disclosed herein are containers comprising the agents and compositions taught herein. Specifically, the container can be a nasal sprayer, a nebulizer, an inhaler, a bottle, or any other means of containing the composition in a form for administration to a mucosal surface. Optionally, the container can deliver a metered dose of the composition.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Nasal Pneumococci Penetrate Olfactory Tissues During Carriage

Materials and Methods
Pneumococcal Strains

The studies employed two encapsulated strains of *S. pneumoniae* EF3030, serotype 19F, and TIGR4 strain, serotype 4 and the avirulent, non-capsular strain R36A derived from the parent strain D39, serotype 2. Avery et al., (1944) J. Exp. Med. 79: 137-158. The EF3030 strain was chosen since it readily colonizes the respiratory tract in the absence of bacteremia (Briles et al., (1992) Infect. Immun. 60: 111-116) and is incapable of sustained bacteremia following intravenous inoculation. The TIGR4 strain was more virulent, but with a modest nasal inoculum colonizes without bacteremia.

Mice

The CBA/CAHN/xid (xid) mouse strain was obtained from the Jackson Laboratory (Bar Harbor, Me.). The mutation in the Bruton's tyrosine kinase gene of these mice results in an inability to respond to thymus-independent type II antigens (Amsbaugh et al., (1972) J. Exp. Med. 136: 931-949; Berning et al., (1980) J. Immunol. 46: 506-513), but permits relatively normal T cell-dependent immune responses. These mice fail to respond to capsular polysaccharides and are reproducibly susceptible to pneumococcal infection. The xid mice were maintained under pathogen-free conditions and were used at 7-12 weeks of age.

Tissue Collection

The blood was collected into a heparinized capillary tube from the retroorbital plexus. Mice were disinfected with 70% ethanol prior to collection of nasal wash (NW), kidney, spleen, and lungs. To prevent blood contamination of the NW an incision was made into the trachea and a 2.0 cm long Tygon tube with an outer diameter of 0.075 cm (Cole-Parmer, Vernon Hills, Ill.) was inserted into the nasopharynx while attached to a syringe filled with Ringer's solution. Fluid from the syringe was expelled through the nose and three drops were collected.

The nasopharyngeal-associated lymphoreticular tissue (NALT), ON/E, OBs and remainder of the brain were obtained as described. van Ginkel et al., (2000) J. Immunol. 165: 4778-4782; Wu et al., (1997) Scand. J. Immunol 46: 506-513. The trigeminal ganglia were carefully excised from the brain with a dissection microscope. The ON/E, OBs, trigeminal ganglia, NALT and cervical lymph nodes CLNs were each homogenized in 0.5 ml Ringer's solution and the brain and kidney each homogenized in 1.0 ml of Ringer's solution.

Quantity of Pneumococci in Tissue Minces/Blood/External Excretions

Eight serial, three-fold dilutions were made of tissues and body fluids in sterile Ringer's solution and plated on blood agar plates containing 4 µg/ml of gentamicin sulfate. The CFU were enumerated 24 hr after plating and incubation in a candle jar. The results were expressed as CFUs/organ, per NW or per ml of blood.

GLS Preincubation of S. pneumoniae Strain EF3030

To block GLS binding sites, $3 \times 10^7$ CFU of S. pneumoniae strain EF3030 were incubated for 30 min on ice with either 20 µg asialo-GM1 from human brain or 125 µg of mixed GLSs (18% GM1, 55% GD1a, 15% GD1b, 10% GT1b, 2% other GLSs) from bovine brain (Calbiochem-Novabiochem Corporation, Inc., La Jolla, Calif.). GLSs were dissolved in PBS and extensively mixed a day prior to use. The amphiphilic GLSs formed micelles in PBS allowing interaction of pneumococci with the carbohydrate moiety. Following incubation, 5 µl per nare was applied nasally to xid mice without further washing. Tissues were analyzed for CFUs four days later.

Detection of S. pneumoniae Pneumolysin Gene by PCR

To detect S. pneumoniae by PCR, tissues were lysed in 1% SDS with 0.1% deoxycholic acid by freeze-thawing, and incubated at 37° C. for 1 hr. Proteins were removed using the cetyltrimethylammoniumbromide/NaCl precipitation method (Ausubel et al., (1987) Current Protocols in Molecular Biology, $2^{nd}$: 2.4.4, which is incorporated herein by reference for teaching of the cetyltrimethylammoniumbromide/ NaCl precipitation method). Ten µg of DNA was used for PCR amplification. The pneumolysin(ply)-specific primers Ply1 5'-ATTTCTGTAACAGCTACCAACGA-3' (SEQ ID NO: 1) and Ply2 5'-GAATTCCCTGTCTTTTCAAAGTC-3' (SEQ ID NO:2) were added to the PCR mixture to amplify a 400 bp fragment. The PCR reaction involved a 5 min denaturation step at 94° C. followed by the amplification cycle: 94° C. (1 min), 55° C. (1 min), and 72° C. (1 min) for 30 cycles. Images of the ethidium bromide stained PCR fragments were collected on an Alpha Imager TM IS-3400 (Alpha Innotech Corporation, San Leandro, Calif.).

Immunofluorescent Staining of OBs with PspA-specific Abs

Mice were nasally challenged with $5 \times 10^5$ CFU of the TIGR4 strain. The OBs were fixed in 10% buffered formalin. Four µm paraffin sections (van Ginkel (2000) J. Immunol. 165: 4778-4782) were stained for PspA family 2 Abs (1:100) by incubating them for 4 hr at room temperature in a humidified chamber. Slides were washed in PBS, stained with biotinylated goat F(ab')2 anti-rabbit IgG (1:200) (Southern Biotechnology Associates, Inc., Birmingham, Ala.), washed and stained with streptavidin-FITC (1:100) (BD-PharMingen, San Diego, Calif.). Fluorescent images were collected with a Nikon microscope using a DEI-750 CE digital color video camera (Optronics, Goleta, Calif.) and processed with the Scion Image software (Scion Corporation, Frederick, Md.).

Statistics

The data are expressed as the mean±one standard error and the results were compared by statistical analysis to determine significant differences in CFUs using the unpaired Mann Whitney two sample rank test or student t-test.

Results

The Role of the Pneumococcal Capsule in Nasal Colonization and CNS Invasion

To examine the up-take of pneumococci through primary sensory olfactory neurons, the ability of EF3030 and a non-encapsulated strain R36A to colonize the nasal tract and enter the CNS were measured at days 1 and 4 (FIG. 1). Although high CFU for both strains were observed in the ON/E on day 1, the R36A were largely absent by day 4 from the ON/E and all other tissues, consistent with earlier results indicating that some capsule is required for prolonged colonization. Magee and Yother (2001) Infect. Immun. 69: 3755-3761. EF3030 showed a clear presence in the OB and brain on both days and were present in high numbers in the NWs and NALT on day 4. These findings were consistent with axonal transport of EF3030 pneumococci into the OBs and brain after nasal challenge.

Kinetics of Nasal Colonization and CNS Invasion

Figure 2A:
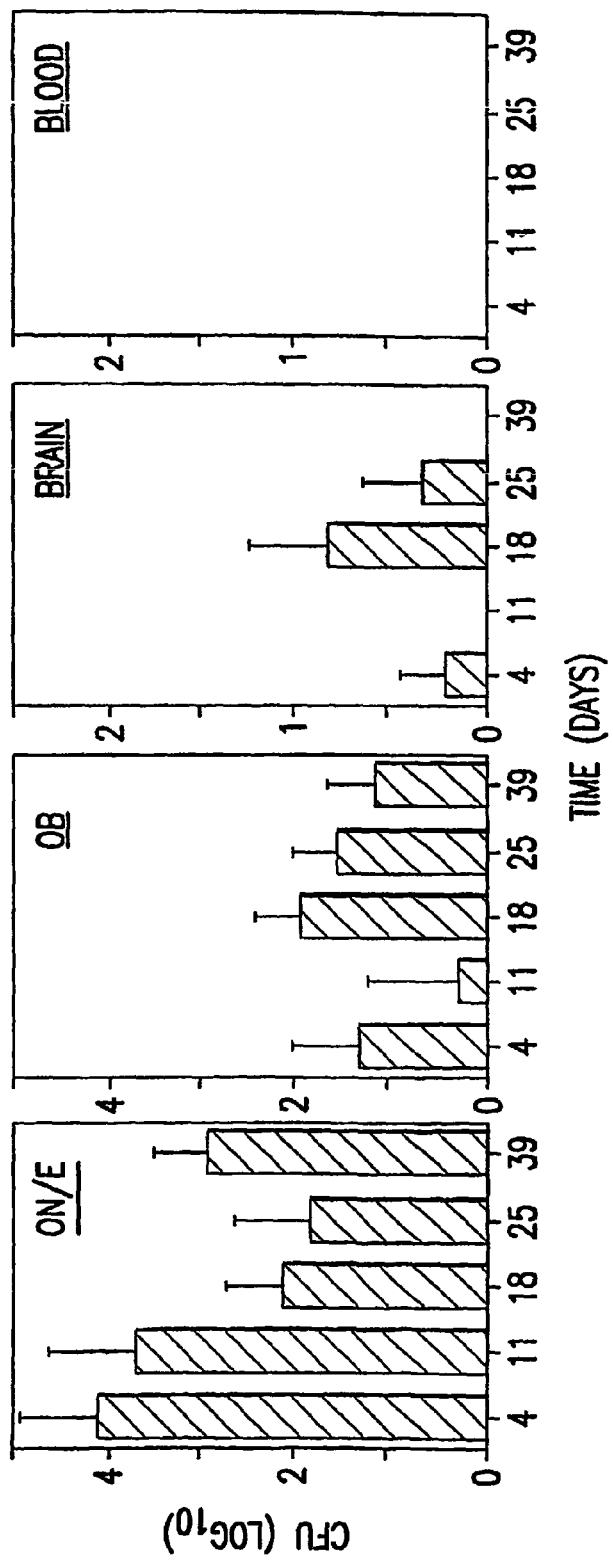
FIG. 2 shows the kinetics of organ distribution of *S. pneumoniae* strain EF3030 CFUs after nasal challenge. The ON/E, OBs, brain, blood, NW, NALT, CLN, and lung tissues were collected on days 4, 11, 18, 25, and 39 and were analyzed for the presence of *S. pneumoniae*. An aliquot of $3\times10^6$ CFU of *S. pneumoniae* resulted in the colonization of the nasal tract and a subsequent infection of the OBs. The 0 value on the Y-axis represents the absence of detectable CFUs. Indicated are the mean CFU+SE of three separate experiments. Each time point represents 10 mice with the exception of day 39, which represents 5 mice.
Figure 2B:
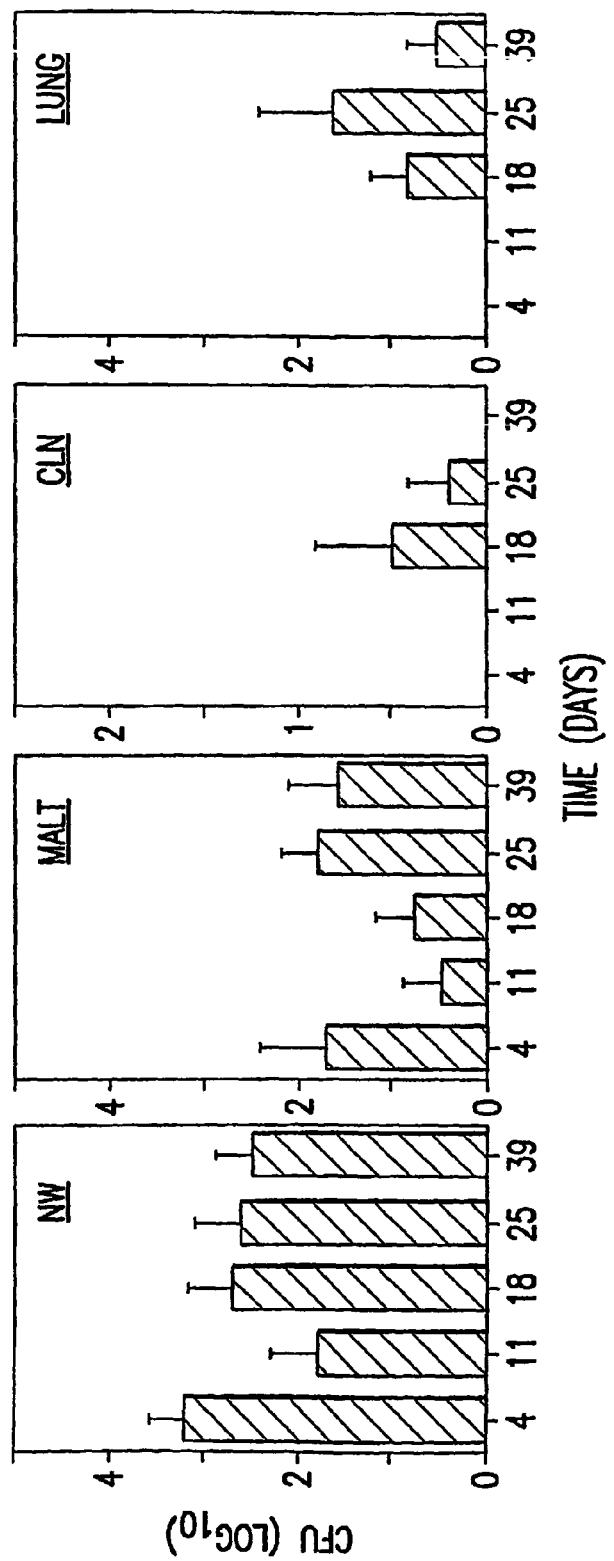

EF3030 was maintained in the ON/E, OBs, NWs, and NALT at all time points over the 39 days of observation (FIG. 2). Much lower numbers of CFU were seen in the brain and CLN, and those CFU present were generally seen at 18 and 25 days. Interestingly, the lungs did not exhibit pneumococci except at day 1 (FIG. 1) and at days 18, 25 and 39 (FIG. 2). Bacteremia did not contribute to the neuronal tissue distribution, since no CFU were detected in the bloodstream of mice during any of the experiments performed with strain EF3030 at the nasal dose used (FIG. 2). Blood was monitored for bacteremia at 1, 3, 6, 12 and 24 hr after nasal application and every subsequent day for one week. No bacteria were detected in the blood.

S. pneumoniae Infection of Trigeminal Ganglia

The trigeminal neurons innervate the nasopharynx and thus, S. pneumoniae would be expected in the trigeminal ganglia after infection of the nasal mucosa. To test this, various tissues and blood were isolated four days after inoculation and analyzed for the presence of EF3030 in new experiments. The EF3030 strain was detected in ON/E and OBs and in trigeminal ganglia (Table 3). This finding further supported that asialo-GM1 function as receptors for neuronal targeting by S. pneumoniae. Other GLSs likely play a role as well.

Table 3 shows the distribution of S. pneumoniae strain EF3030 in various tissues after nasal delivery. Tissues were isolated on day 4 after nasal application of $1 \times 10^7$ CFUs of strain EF3030. Blood (50 µl), ON/E, OBs, and brain tissue minces were diluted and then plated on blood agar. The trigeminal ganglia were pooled, homogenized and then plated on this medium. Indicated are the mean pneumococcal CFUs±SE of 5 mice and are representative of three separate experiments. In the brain and blood no pneumococci were detected.

TABLE 3

| Tissue | Mean CFU ($Log_{10}$) | SE |
| --- | --- | --- |
| Brain | 0 | |
| Olfactory bulbs | 1.38 | 0.61 |
| ON/E | 4.93 | 0.42 |
| Blood | 0 | |
| Trigeminal ganglia | 2.08 | (pooled) |

Gangliosides Inhibit Pneumococcal Colonization

Figure 3A:
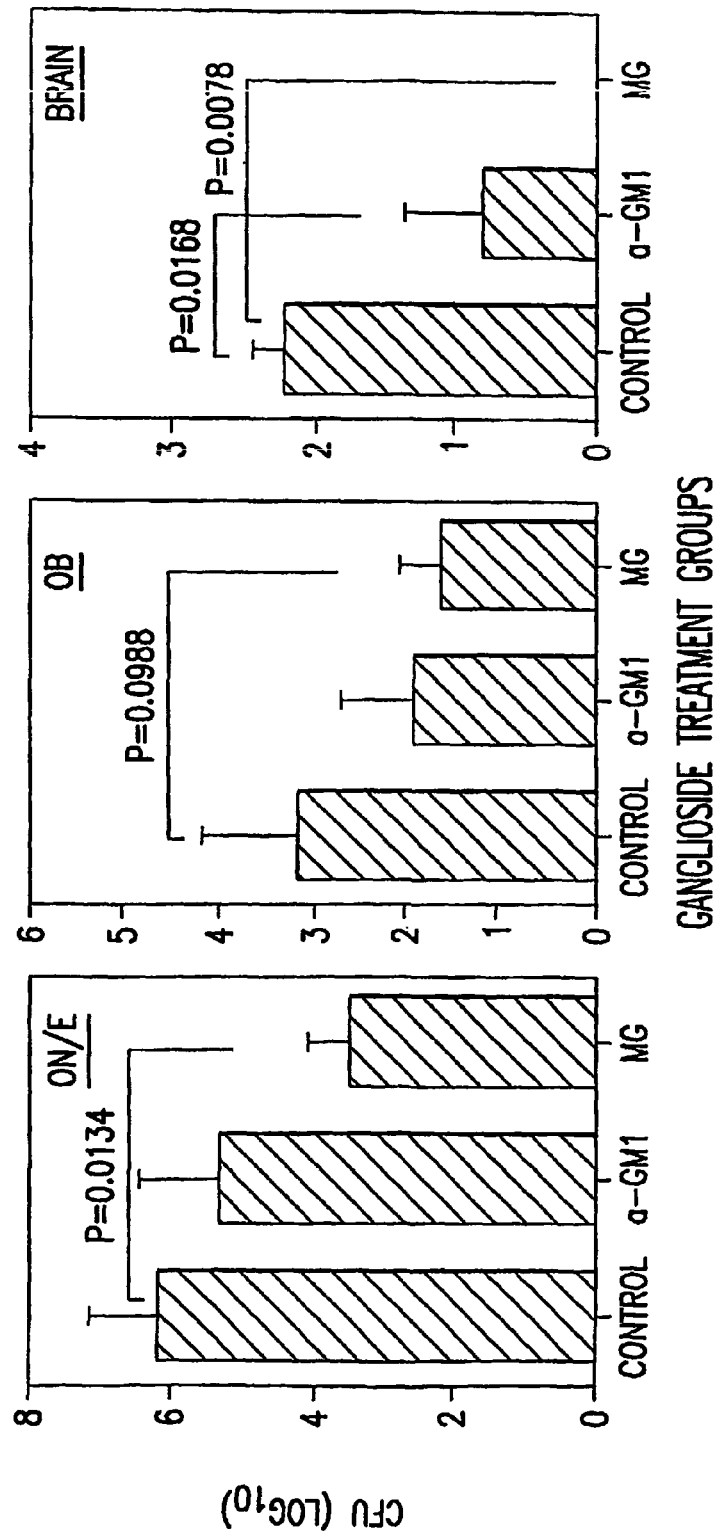
FIG. 3 shows the distribution of *S. pneumoniae* strain EF3030 following preincubation with GLSs. Aliquots ($3\times10^7$ CFUs) of *S. pneumoniae* were incubated for 30 minutes with 20 µg asialo-GM1 (a-GM1) or 125 µg of mixed GLSs (MG) prior to nasal application. The ON/E, OBs, brain and NW, NALT and lungs were collected four days later and analyzed for numbers of *S. pneumoniae*. The 0 value on the Y-axis represents the absence of detectable CFUs. Indicated are the mean+one SE of 5 mice and the P-values were obtained following statistical analysis. The data are representative of two separate experiments.
Figure 3B:
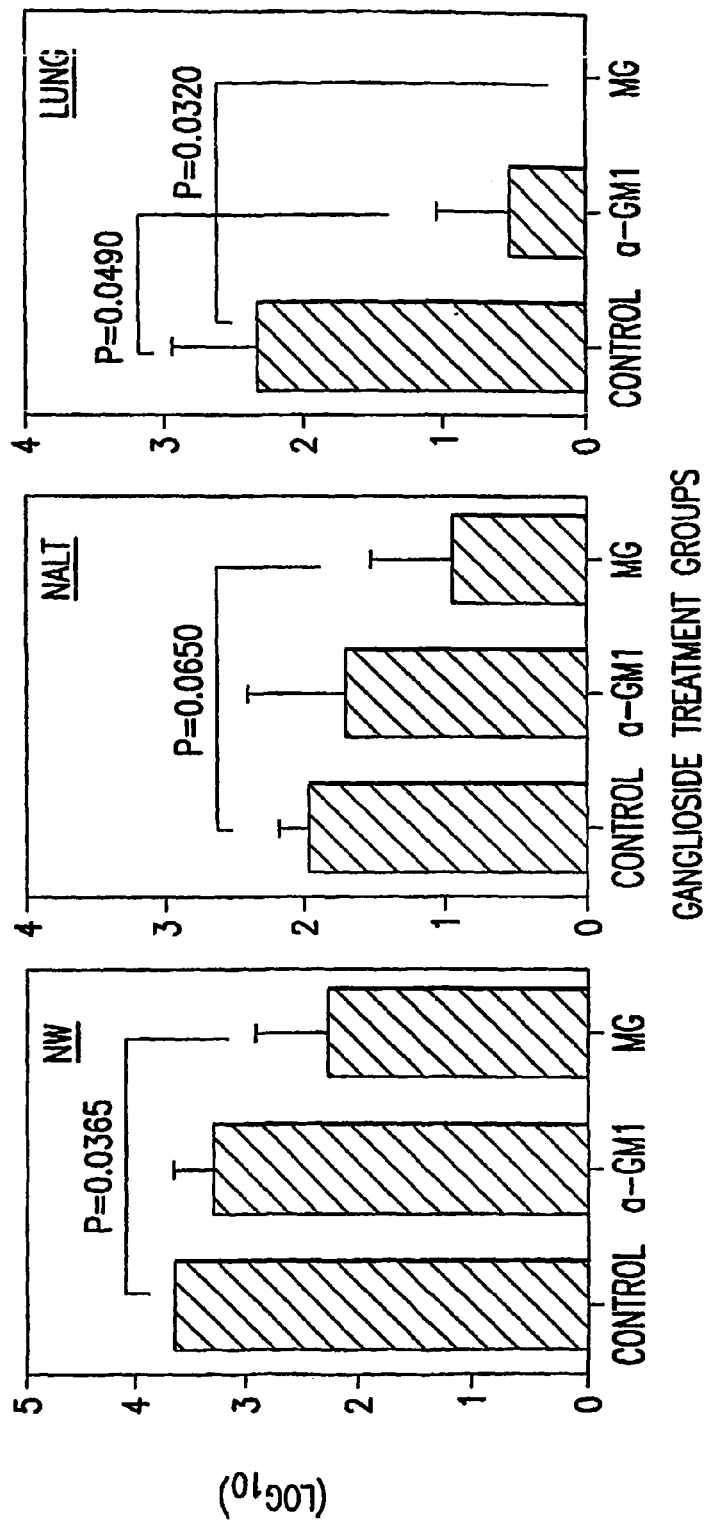

The EF3030 strain was incubated with asialo-GM1 or mixed GLSs micelles in PBS prior to nasal application. The GLS mixture displayed the strongest inhibitory effect and reduced CFU in NW by 10 fold (P=0.0365) when assessed four days after nasal application. The largest decline in CFU as a result of mixed GLS preincubation was seen in the ON/E (617-fold decline; P=0.0134). Just as striking were the differences in the lungs (P=0.0320) (FIG. 3B) and CNS tissue (P=0.0078) (FIG. 3A), where an average of 204 and 166 CFU were present in the controls, while pneumococci were undetectable (detection limit=3 CFU) when incubated with GLSs. The asialo-GM1 preincubation was less efficient than mixed GLSs but still reduced colonization 25- and 63-fold in CNS (FIG. 3A) and lungs (FIG. 3B), respectively. The lungs were infected by inhaled pneumococci and their attachment to asialo-GM1, relatively abundantly present in lungs, was apparently inhibited by GLSs. This indicates that GLSs play a role in the initial attachment to epithelial cells. GLS treatments did not change pneumococcal viability. No pneumococci were detected in the blood during these experiments. Thus, GLSs constitute an important target for pneumococcal attachment to neuro-epithelium of the nasal tract and infection of lungs and CNS.

Detection of S. pneumoniae Accumulation in the OBs Following Nasal Challenge

The numbers of EF3030 in OBs were generally too low to make visualization of bacteria by microscopy feasible. To visualize S. pneumoniae in the OBs after nasal application, a more virulent strain, TIGR4, was used. Blood samples were tested from representative mice at 1, 3, 6, 12 or 24 hrs after challenge and on every subsequent day. No bacteremia was observed. The mice were sacrificed one week after challenge and tissues were analyzed for CFU (FIGS. 4A and 4B). A dose of only $5 \times 10^5$ TIGR4 CFU resulted in ~300 CFU in the OBs (FIG. 3). The pneumococci were visualized by staining with PspA-specific Abs in the OBs (FIG. 4D-F). Pneumococci were detected in the OBs, i.e., the glomerular layer (FIG. 4F) and the external plexiform layer (FIG. 4E) of challenged mice. Pneumococci were absent in the OBs of control mice (FIG. 4D).

The TIGR4 strain was also detected by PCR amplification of the pneumolysin gene from the NWs, ON/E and OBs 6 days after nasal administration (FIG. 4C). No PCR-detectable pneumococci were present in the bloodstream taken at this interval, or in any samples from non-infected mice.

Example 2

The Role of Pneumococcal-NanA in Nasopharyngeal Carriage and Targeting of the CNS NanA mutants were generated in three strains of S. pneumoniae differing both in genetic background and localization of NanA. Strains EF3030 (type 19F) and D39 (type 2) both express a NanA that is covalently attached to the cell wall whereas the TIGR4 strain (type 4) expresses a truncated NanA that is secreted into the environment.

The role of NanB in colonization was also assessed.
Bacterial Strains and Growth Conditions.
Strains used in this study are listed in Table 4.

TABLE 4

| Strains, plasmids, and primers | genotypes or primer sequences | |
|---|---|---|
| TOP 10F' | E. coli strains | |
| S. pneumoniae strains | | |
| TIGR4 | capsular serotype 4* | |
| EF3030 | capsular serotype 19F† | |
| D39 | capsular serotype 2‡ | |
| JPC001 | D39/NanA- (insertion duplication)§ | |
| JW001 | TIGR4/nanA- (insertion-duplication mutant) | |
| JW002 | TIGR4: nanA deletion | |
| JW003 | TIGR4 nanB- (insertion-duplication mutant) | |
| JW004 | TIGR4 nanAB- (insertion-duplication double mutant) | |
| SAM001 | EF3030 nanA- (insertion-duplication mutant) | |
| SAM003 | EF3030 nanAB-(insertion-duplication double mutant) | |
| Plasmids | | |
| pSF152 | Suicide vector for deletion of nanB; spectinomycin resistance | |
| pCR4-TOPO | Cloning vector; ampicillin and kanamycin resistance | |
| Primers | | |
| NAF1 | 5- CGCGGATCCTCATACTGGGTTAGGAAAGTCGTCG-3 | (SEQ ID NO: 6) |
| NAF 1.1 | 5- GGAATTCCATATGCCGACAGCAGAACTACCTAAAGGC-3 | (SEQ ID NO: 7) |
| NAW 1.1 | 5- GGAATTCCATATGCTGGCAAATGAAACTCAACTTTCGGGGG-3 | (SEQ I NO: 8) |

TABLE 4-continued

| Strains, plasmids, and primers TOP 10F' | genotypes or primer sequences E. coli strains | |
|---|---|---|
| NAP1.1 | 5- CGCGGATCCATCGGCTTTGACCATCGGAG-3 | (SEQ ID NO: 9) |
| NAP1.2 | 5- GGAATTCCATATGCGTATTCCAGCACTTCTCAAGACAG-3 | (SEQ ID NO: 10) |
| nanBF | 5- GGAACATTACCTCGCAAAAGG-3 | (SEQ ID NO: 11) |
| nanBR | 5- TACCCGCAGGCATAACATC-3 | (SEQ ID NO: 12) |

*Tettelin et al. (2001) Science 293: 498-506.
†Briles et al. (2003) J Infect Dis 188: 339-348
‡Avery et al. (1979) J. Exp. Med 149: 297-326; McDaniel et al. (1987) Microb. Pathog. 3: 249-260.
§Berry et al. (2000) Infect. Immun. 68: 133-140.

All pneumococcal strains were stored at −80° C. in 10% glycerol and cultured by transfer to blood agar plates and incubated at 37° C. in a 5% CO2 atmosphere overnight. Cultures of pneumococci were grown in Todd-Hewitt Medium containing 0.5% yeast extract to an OD660 of 0.5 and stored frozen in aliquots at −80° C. in the same broth supplement to 10% with sterile glycerol. Mutants carrying antibiotic resistant inserts were grown in the appropriate antibiotics to insure stability of the mutations.

Construction of nanA Mutants.

NanA mutant strains JW001, SAM001, and JCP001 of parental backgrounds TIGR4, EF3030 and D39, respectively, were derived through insertion duplication mutagenesis techniques (Yother et al. (1992) J. Bact. 174:610-618, which is incorporated by reference herein in its entirety for the techniques taught therein) (Table 4). Strains TIGR4 and EF3030 were used as recipients for the transformation of donor chromosomal DNA prepared from the isogenic nanA strain D39 (Berry et al. (2000) Infect. Immun. 68:133-140). In each case, the mutants were backcrossed three times-into the parental strain. The D39 mutant was also backcrossed three times into our D39 parental strain to make sure it was isogenic with the parental strain used in these studies. The mutation of D39 was made by insertion duplication mutagenesis allowed the deletion of all but an N-terminal fragment of about 650 amino acids of the mature protein (Berry et al. (2000) Infect. Immun. 68:133-140). A TIGR4/nanB isogenic mutant was constructed using insertion duplication mutagenesis techniques (Balachandran et al (2002) Infect. Immun. 70:2536-2534; Yother et al. (1992) J. Bact. 174:610-618). A 461-bp internal portion of nanB was amplified using the primers: nanBF and nanBR (Table 1), PCR was carried out using Taq PCR Mastermix (Invitrogen) and 30 cycles at 95° C. 1 min., 45° C. 1 min., 72° C. 1 min. The fragment was cloned into pSF152. Transformation of the TIGR4 strain with the plasmid DNA were as before (Balachandran et al. (2002) Infect. Immun. 70:2526-2534). A nanA/nanB-TIGR4 double mutant was derived by transformation of the nanBmGR4 mutant with chromosomal DNA prepared from strain JW001.

Mouse Virulence Assays.

Female 6-12 week old CBA/CaHN-XID/J (CBA/N) mice were obtained from The Jackson Laboratory (Bar Harbor, Mass.). The mutation in the Bruton's tyrosine kinase gene of these mice results in an inability to respond to thymus-independent type II antigens but permits relatively normal T cell-dependent immune responses (Amsbaugh et al. 1972 J Exp Med. 136:931-949; Briles et al. 1986 Curr. Top. Microbiol. Immunol. 124:103-120; Potter et al. 1999 Int. Immunol. 11:1059-64; Wicker and Scher 1986 Curr. Top. Microbiol. Immunol. 124). These mice fail to respond to capsular polysaccharides and are reproducibly susceptible to pneumococcal infection (Briles et al. 1986 Curr Top. Microbiol. Immunol. 124:103-120; Briels et al. 1981 j. Exp. Med. 153: 694-705). The x-linked immunodeficient (xid) mice were maintained under pathogen-free conditions and were used at 7-12 weeks of age. Frozen infection stocks containing a known concentration of viable cells were diluted in lactated Ringer's solution. Mice were then infected intranasally (I.N.) with approximately $5 \times 10^5$-$1 \times 10^6$ cells in a volume of 10 μl as described (Wu et al. 1997b Microb. Pathog 23:127-137).

Tissue Collection.

All mice were euthanized prior to performing nasal washes and tissue collection. The blood was collected into a heparinized capillary tube from the retroorbital plexus. Mice were disinfected with 70% ethanol before collection of nasal wash (NW), nasal tissue (including the olfactory epithelium (NT) olfactory bulbs (OB), and brain. These fluid and tissues were obtained as described above. To prevent blood contamination of the NW, an incision was made into the trachea and a 2.0-cm-long Tygon tube with an outer diameter of 0.075 cm (Cole-Parmer) was inserted into the nasopharynx while attached to a syringe filled with Ringer's solution. Fluid from the syringe was expelled through the nose, and three drops were collected. The ON/E and OB were each homogenized in 0.5 ml of Ringer's solution while the remainder of the brain was homogenized in 1.0 ml of Ringer's injection solution.

Quantitation of Viable Pneumococci

Eight serial, 3-fold dilutions were made of tissues and body fluids in sterile Ringer's solution and plated on blood agar plates containing 4 μg/ml gentamicin sulfate. The colony forming units (CFU) were enumerated 24 h after plating and incubation at 37° C. in a candle jar. The assay used for neuraminidase activity has been previously described (Lock et al 1988 Microb Pathog 4:33-43, which is incorporated herein by reference in its entirety for the assay methods). Significance of results was assessed by analysis with a two sample Mann-Whitney rank test making comparisons between wild type pneumococci and mutant pneumococci.

In Vitro Studies

The ability of the TIGR4, and its nanA and nanB mutants to bind to specific gangliosides is measured. The gangliosides used include mixed gangliosides, asialo-GM1, GM1, GD1a, GD1b, GT1 (Calbiochem) and the GM3 ganglioside (Sigma). The GM3 ganglioside lacks the terminal or internal Gal-NAcβ1-4Gal sequence involved in pneumococcal binding and is used as a negative control. These mixed, mono-, di- or tri-sialic acid containing gangliosides bind readily to ELISA plates. Initial data following short-term incubation with the TIGR4 strain indicates that pneumococci bind to asialo-GM1-coated plates but not to BSA-, GM-3, or GM1-coated plates. Using ganglioside-coated plates, the ability to attach to these plates by wildtype TIGR4 strain, the stable opaque and transparent phase variants of the TIGR4 strain, the nanA, nanB, and nanA/nanB mutant strains is compared. These analyses include short-term incubation (1 hr) and extended incubations (24 hrs) on ganglioside-coated plates. Attached pneumococci are removed from the ganglioside plates by short incubation (10-15 min.) in Todd Hewitt medium containing 0.5% yeast extract followed by repeated pipetting and plating the released bacteria on blood agar plates. Alternatively 41° C. Todd Hewitt broth agar containing 0.5% yeast extract is poured on top of the attached pneumococci and the colonies are counted through the bottom of the plate. Controls include plates with no pneumococci and plates with no gangliosides but with pneumococci.

Subsequent to testing ganglioside binding, different cell lines are tested for their ability to attach pneumococci to their cell surface and internalize them. These studies focus on the rat neuronal pheochromocytoma cell line PC12 (ATCC) and the macrophage cell line P388D1. These two cell lines were chosen because of their specific attributes. The P388D1 cell line expresses high affinity PAF-R (Valone (1988) J. Immunol. 140: 2389-2394), which has been reported to be present on microglia. The PC12 cell line does not express detectable PAF-R. Brewer et al., (2002) J. NeuroChem 82: 1502-1511. Between $10^2$-$10^5$ pneumococcal CFU are added to these cell lines grown in 6 well or 24 well tissue culture plates and are incubated at 37° C. for between 15 min. to 6 hrs after which the cells are extensively washed and adherent pneumococci analyzed. To determine internalization into the cells a 2 hr wash with penicillin and gentamicin is performed prior to plating the cells on blood agar or over-laying them with 41° C. Todd Hewitt broth agar containing 0.5% yeast extract. The two cell lines used reflect in vivo expression of the PAF-R normally observed in the CNS. While activated microglia abundantly express this receptor as does the P388D1 cell line, the PAF-R receptor is either absent on neuronal cells, such as the PC12 cell line, or is only expressed at low levels by discrete neuronal subpopulations. Mori et al., (1996) J. Neurosci 16: 3590-3600; Bennett et al., (1998) Cell Dath Differ. 5: 867-875. Adherence of pneumococci to both cell lines would indicate that the PAF-R is not essential for adherence and alternative receptor exist. The TIGR4 opaque and transparent variants and the nanA-, nanB-mutants and nanA/nanB double mutant are tested for adherence to these cell lines relative to that observed with the wildtype TIGR4 strain. To further analyze the role of PAF-R versus gangliosides in pneumococcal adherence, the COS-7 cell line (Gerard and Gerard (1994) J. Immunol. 152: 793-800; Honda et al., (1992) J. Lipid Med. 5: 105-107), which lack PAF-R, are transfected with the human PAFR open reading frame of 1029 bp using the pcDNA3.1/GS plasmid as previously reported (Brewer et al., (2002) J. Neuro Chem 82: 1502-1511, which is incorporated herein by reference in its entirety for the methods taught therein) and tranfected using Transfast reagent (Promega). The plasmid alone is used as a control and the parameters influencing pneumococcal adherence are analyzed in the presence or absence of PAF-R. This experiment provides unequivocal data regarding the importance of PAF-R in adherence. Any adherence in PAF-R deficient cell lines is mediated by gangliosides and is subsequently blocked by preincubation with gangliosides. To further address the ability of pneumococci to attach to and penetrate epithelial cells the Detroit 562 human pharyngeal epithelial cell line (ATCC) and A549 human pulmonary epithelial cell line (ATCC) is employed using a transwell system. The Millicell®-PCF Culture (Millipore, Billerica, Mass.) plate inserts are used to grow the epithelial cell lines to confluency. Confluency is determined by measuring the transepithelial resistance using a Millipore Millicell® electrical resistance system. A resistance of at least 500Ω per $cm^2$ indicates that a fully confluent epithelial monolayer is achieved. These cells are exposed to pneumococci to test their ability to attach to, enter into and penetrate this epithelial layer. To distinguish attachment versus internalization the epithelial cells are washed and incubated for 2 hrs with medium containing penicillin and gentamycin. The initial focus is on the TIGR4 strain, its nanA and nanB mutants, and the double mutant. Stable transparent and opaque variants of the TIGR4 strain have been generated by sequential passages until stable variants were obtained that did not reverse following in vivo challenge. These TIGR4 variants are compared for their ability to adhere to, enter and tranverse epithelial cells. Wells are loaded with $10^3$-$10^6$ CFU/well in EMEM media. At 0.5, 1, 2, 4, 8, and 24 hrs cultures are harvested both above and below the epithelial layer and analyzed for CFU. The cell layers are washed 5-6 times prior to overlaying the cells with Todd-Hewitt broth supplemented with 0.5% yeast extract and 0.5% agar cooled to 41° C. to determine the pneumococcal CFUs associated with the monolayer. The plates are incubated overnight at 37° C. and 5% CO2 after which the CFU are counted. The cell lines are analyzed for expression of the PAF-R. Total RNA derived from these cell lines are analyzed by RT-PCR using the two primers, PAF-1 (5'-CCGATACACTCTCTTC-CCGA-3' (SEQ ID NO:3); nucleotides 151 to 170) and PAF-2 (5'-ACAGTTGGTGCTAAGGAGGC-3' (SEQ ID NO:4); nucleotides 970 to 951) resulting in a 838 bp PCR product (Stengel et al., (1997) Arterioscler. Thromb. Vasc. Biol. 17: 954-962, which is incorporated herein in its entirety for the methods taught therein). If the PAF receptor is present PAF receptor inhibitors such as octylonium bromide (Biomol Research Laboratories, Inc. Plymouth meeting, PA) or PAF (Biomol) are added to the cultures to determine the contribution of the PAF-R on epithelial adhesion and penetration. The octylonium bromide binds with high affinity to the PAF-R Alternatively the above mentioned COS7 cells are used for this purpose and compare pneumococcal adherence in the presence and absence of PAF-R.

The degree of invasiveness of the different pneumococcal strains is correlated with production of inflammatory cytokines in both the apical and basolateral compartment of the Transwell system. The culture supernatants are collected at the various timepoints in both the upper and lower compartment and analyzed by ELISA (1D PharMingen) to determine the concentration of the inflammatory cytolines IL-1β, IL-6, IL-8, IL-10 and TNF-α. The epithelial monolayers are fixed in acetic alcohol and analyzed for the intracellular presence of pneumococci using PspA-specific immunofluerescent staining as previously used for visualization of pneumococci in OBs. Fluorescent images are visualized with a Leica/Leitz DMRB microscope equipped with appropriate filter cubes (Chromtechnology, Battleboro, Vt.) as previously described (Martin et al., (1998) J. Immunol. 160: 3748-3758, which is incorporated herein by reference for the methods taught therein). Images are collected with a C5810 digital color camera (Mamamatsu Photonic System) and processed with Adobe photoshop and IP LAB Spectrum software.

Results

Colonization of NanA and NanB Mutants.

Figure 5:
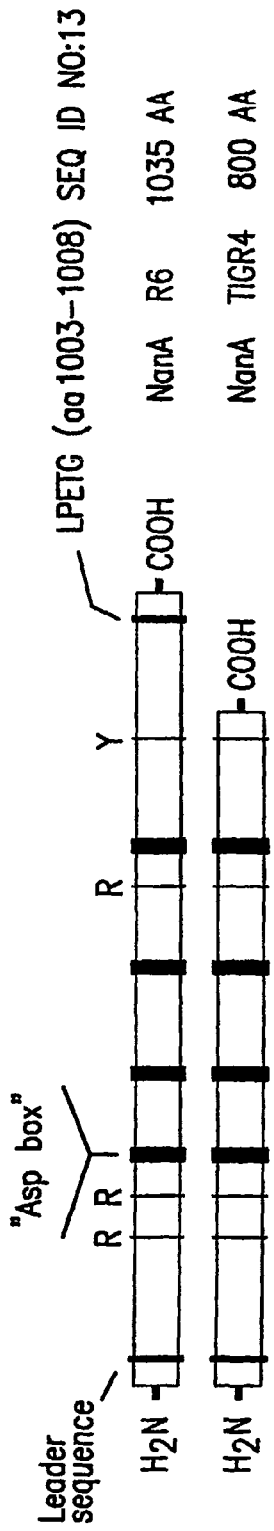
FIG. 5 shows a comparison in the motifs for secreted NanA, TIGR4, and for a R6 (type 2), which has the LPXTG (SEQ ID NO:14) motif for attachment to the cell wall. The TIGR4 gene includes a stop-codon prior to the sequence encoding the LPETG (SEQ ID NO: 13) motif. Without this motif, NanA is secreted into the environment by TIGR4.

The effects of NanA mutations on the ability of *S. pneumoniae* to colonize the nasopharynx of CBA/N mice was assessed by comparing the numbers of pneumococcal cells isolated from nasal washes of mice that had been infected intranasally (i.n.) with those infected with NanA mutant-strains. Three different pneumococcal strains were included, thus, allowing for the effects of NanA mutations to be investigated on strains differing in capsular serotype and genetic background. TIGR4/NanA– (JW001), EF3030/NanA– (SAM001) and D39/NanA– (JCP001) are capsular type 4, 19F and 2, respectively (Table 4). In the case of the capsular type 4 clinical isolate, TIGR4, there is a stop-codon prior to the sequence encoding the LPETG (SEQ ID NO:13) motif. Without this motif, NanA is expected to be secreted into the environment by TIGR4. Examination of the other four pneumococcal-NanA sequences currently available, G54 (type19F), R6 (type 2), Spanish 23F and 670 (type 6B) (Berry et al. Gene 71:299-305; Hoskins et al. 2001 J. Bacteriol 183:5709-17; Tettelin et al. 2001 Science 293:498-506) indicated that they have the LPXTG (SEQ ID NO: 14) motif for covalent attached to the cell wall (FIG. 5). Therefore, strains included here provided a comparison for mutations in strains where NanA is secreted and where it is surface bound.

Figure 6A:
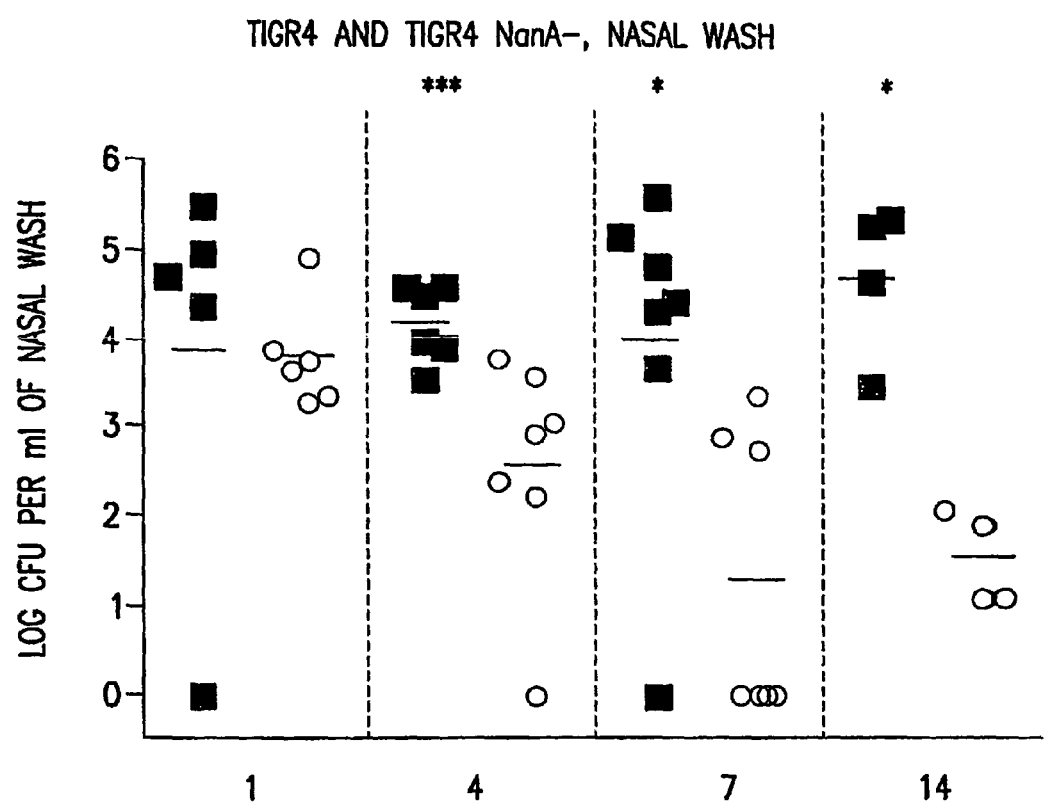
FIG. 6A shows the kinetics of viable pneumococci in the nasal wash of CBA/N mice infected i.n. with the *S. pneumoniae* parental strain TIGR4 (■) or the NanA isogenic mutant TIGR4/nanA− (○). Each point represents the total number of bacteria per ml of nasal wash fluid from each mouse. *$P<0.05$; $P<0.01$; *$P<0.005$, compared with mice inoculated with TIGR4.
Figure 6B:
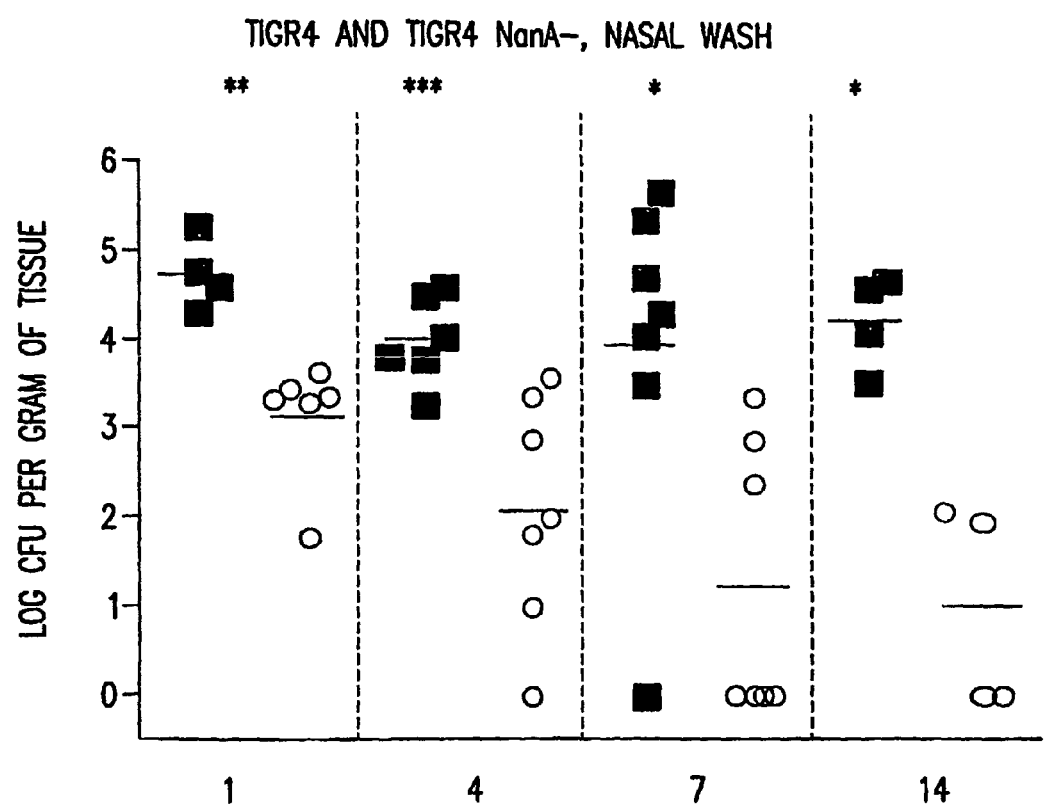
FIG. 6B shows nasal colonization kinetics in CBA/N mice infected i.n. with the *S. pneumoniae* parental strain TIGR4 (■) or the NanA isogenic mutant TIGR4/nanA− (○). Each point represents the total number of bacteria per gram of tissue from each mouse. *$P<0.05$; $P<0.01$; *$P<0.005$, compared with mice inoculated with TIGR4.
Figure 6C:
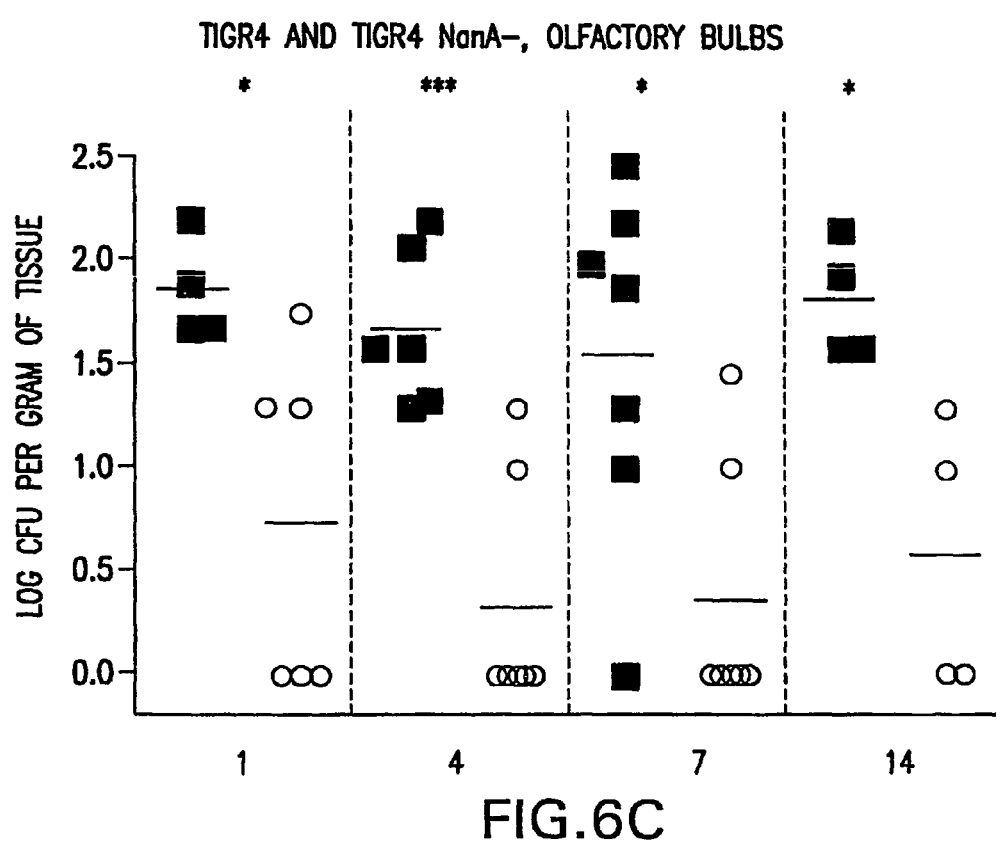
FIG. 6C shows the kinetics of CFU in the olfactory bulb of CBA/N mice infected i.n. with the *S. pneumoniae* parental strain TIGR4 (■) or TIGR4/nanA− (○). Each point represents the total number of bacteria per gram of tissue from each mouse. *$P<0.05$; $P<0.01$; *$P<0.005$, compared with mice inoculated with TIGR4.
Figure 7A:
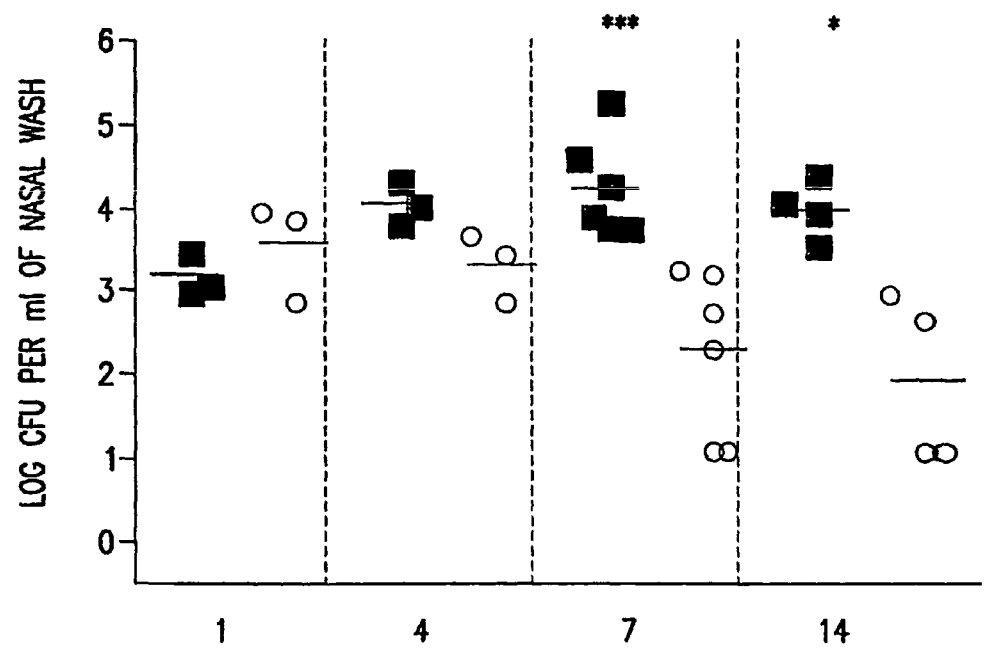
FIG. 7A shows nasal colonization kinetics in CBA/N mice infected i.n. with the *S. pneumoniae* parental strain EF3030 (■) or EF3030/nanA− (○). Each point represents the total number of bacteria per ml of nasal wash from each mouse. *$P<0.05$; $P<0.01$; *$P<0.005$, compared with mice inoculated with EF3030.
Figure 7B:
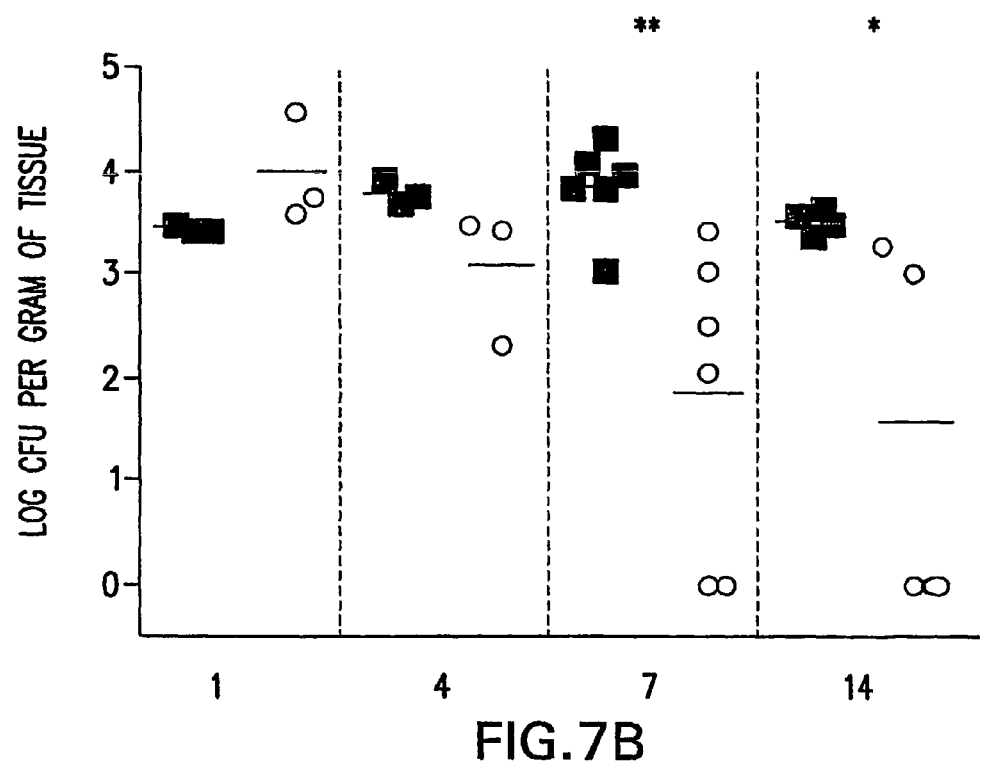
FIG. 7B shows nasal colonization kinetics in CBA/N mice infected i.n. with the *S. pneumoniae* parental strain EF3030 (■) or EF3030/nanA− (○). Each point represents the total number of bacteria per gram of tissue from each mouse. *$P<0.05$; $P<0.01$; *$P<0.005$, compared with mice inoculated with EF3030.
Figure 7C:
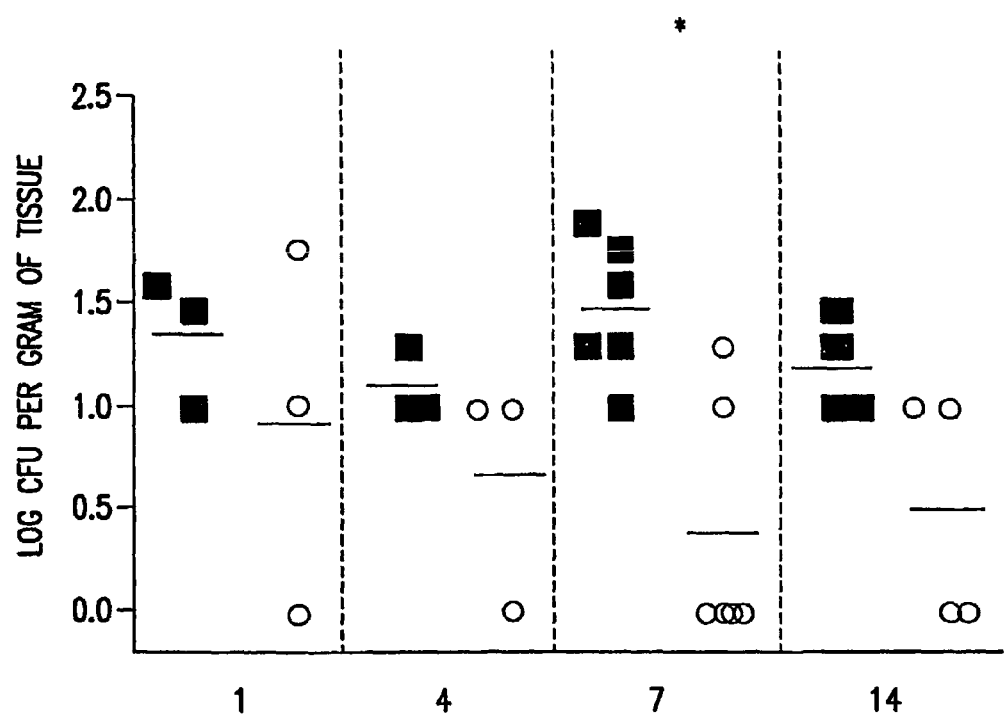
FIG. 7C shows nasal colonization kinetics in CBA/N mice infected i.n. with the *S. pneumoniae* parental strain EF3030 (■) or the NanA isogenic mutant EF3030/nanA− (○). Each point represents the total number of bacteria per gram of tissue from each mouse. *$P<0.05$; $P<0.01$; *$P<0.005$, compared with mice inoculated with EF3030. When wild type and mutant data are pooled for all time points the comparison between EF3030 and EF3030 NanB− was $P=0.001$.

A dramatic decrease in colonization was observed in the NanA mutants of both TIGR4 and EF3030 (FIGS. 6 and 7).

Figure 8:
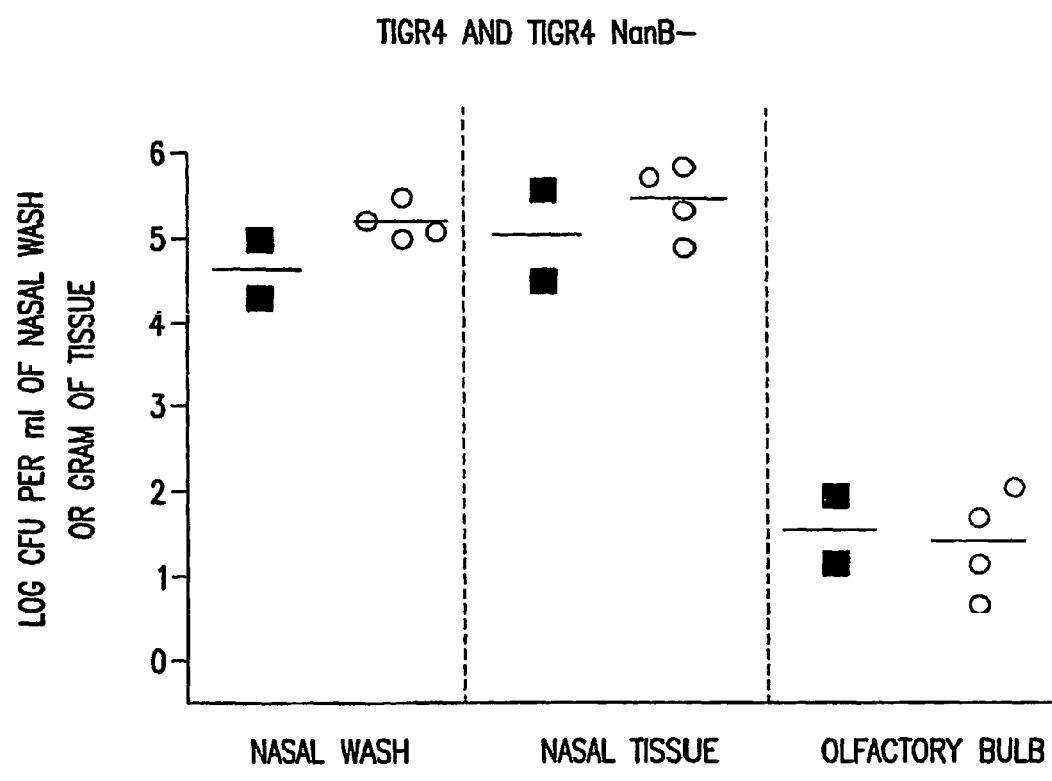
FIG. 8 shows nasal colonization kinetics in CBA/N mice infected i.n. with the *S. pneumoniae* parental strain TIGR4 (■) or TIGR4/nanB− (○) at 4 days post inoculation. Each point represents the total number of bacteria per ml of nasal wash or gram of tissue from each mouse. In no case was the difference between TIGR4 and TIGR4/nanB− statistically significant.
Figure 9:
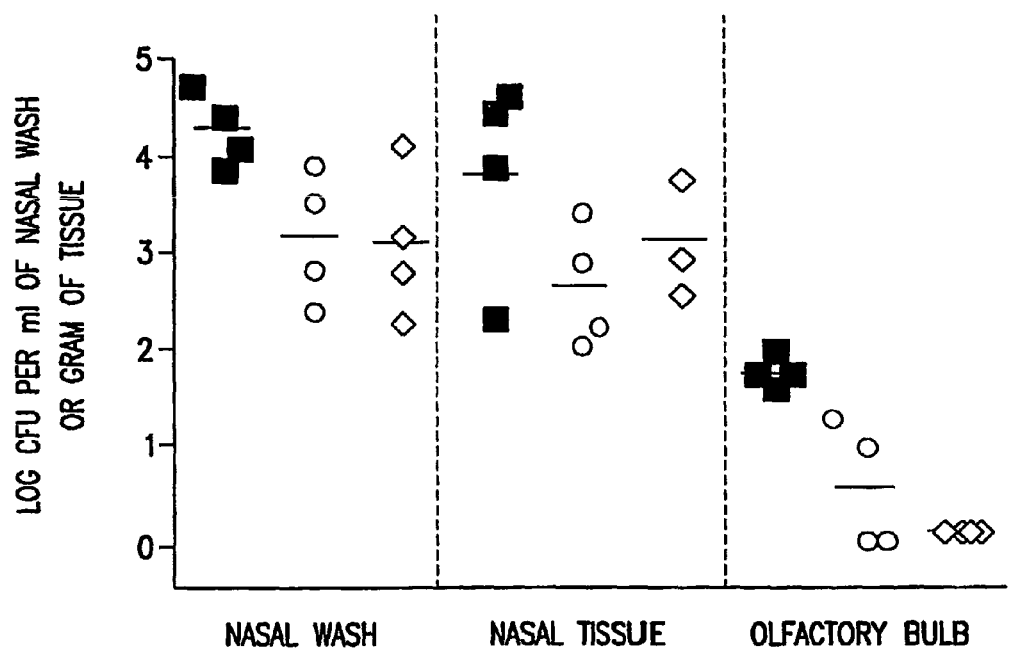
FIG. 9 shows nasal colonization kinetics in CBA/N mice infected i.n. with the *S. pneumoniae parental* strain TIGR4 (■) TIGR4/nanA− (○) or TIGR4/AB− at 4 days post inoculation. Each point represents the total number of bacteria per ml of nasal wash or gram of tissue from each mouse. In no case was the difference between TIGR4/nanA− and the double mutant TIGR4/nanAB− statistically significant.
Figure 10:
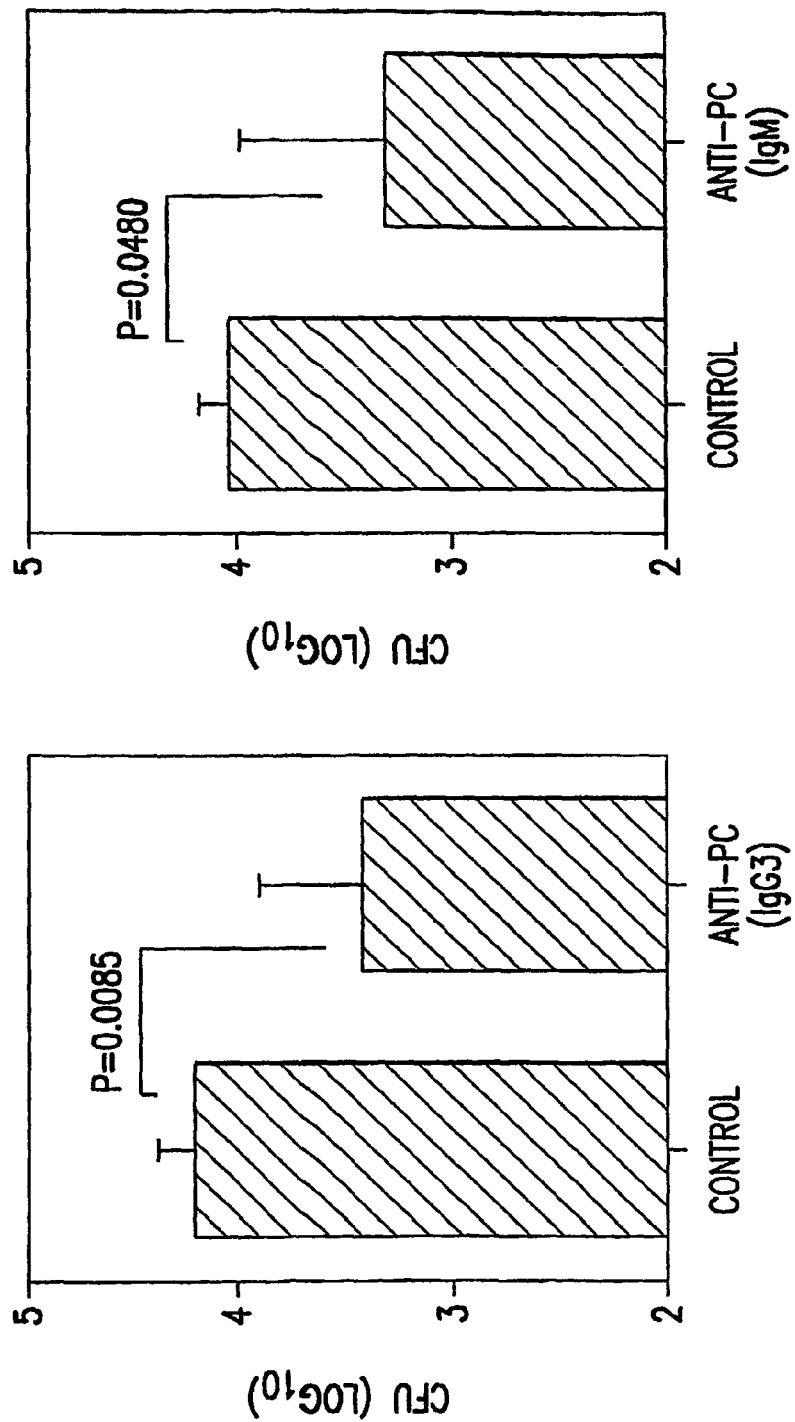
FIG. 10 shows inhibition of nasal colonization of *S. pneumoniae* by anti-phosphocholine-specific monoclonal antibodies after nasal challenge. Inhibition of nasal colonization of *S. pneumoniae* by anti-PC-specific mAbs after nasal challenge. A total of $1 \times 10^6$ CFU of the TIGR4 strain were incubated with 5 μg of anti-PC mAbs of either the IgG3 subclass or IgM isotype. A total of 5 μl was administered per nare. Indicated are the CFU in 500 μl nasal wash respectively 9 and 12 hours after application. Indicated are the mean+SD of five mice per group.

S. pneumoniae expresses another neuraminidase, NanB. A similar degree of homology is shared between NanB relative to NanA. NanB shares 43% homology (24% identity) with NanA. Shared residues between the proteins have suggested that it is a sialidase (Berry et al. 1996 J. Bacteriol. 178:4854-4860). NanB has been found to have a pH optimum of 4.5 as compared to the pH optimum of NanA between 6.5 and 7. Even at its optimal pH, NanB is about 1/100th as active as a sialidase as is NanA at its pH optimum. Even so, to see if there is a requirement of NanB for colonization and direct invasion of the CNS, strains TIGR4/NanB– (JW002), a mutant was constructed in the TIGR4 genetic background deficient in NanB as well as strain TIGR4/NanAB– (JW003), which is deficient in both NanA and NanB expression. Infection of mice with JW002 resulted in a level of colonization nearly identical to the TIGR4 strain (FIG. 8). Moreover, no significant reduction in colonization occurred in the double mutant (JW003) relative to the NanA mutant (FIG. 9).

Entrance of Pneumococci into the CNS.

In order to track the movement of S. pneumoniae to the nasal tissue (including the olfactory nerves) the olfactory bulb and the remainder of the brain were tested for the presence of S. pneumoniae. NanA mutants, regardless of genetic background, were found in significantly reduced numbers relative to wild type strains in the nasal tissue and olfactory bulb. At the time of sacrifice, all mice were bled and none exhibited detectable pneumococci in the blood (<12 CFU/ml blood), indicating that pneumococci move directly into the CNS tissue from the nasal cavity. The NanB mutant had no effect on the entry of the pneumococci into the nasal tissue or the olfactory bulb (FIG. 8).

NanA mutants are clearly attenuated in their ability to colonize and persist in the nasopharynx and the CNS. This was observed in strains differing in both capsular serotype and attachment of NanA to the surface. Although NanA is but one of many surface structures that influence the intimacy between the bacterial cell surface and the host, its involvement is essential in nasal carriage as well as targeting of pneumococci to the CNS. Disruption of NanA significantly reduced colonization and targeting to the CNS. This result was observed in both TIGR4 and EF3030.

Strain EF3030 (type 19F) colonizes the nasopharynx with great efficiency for over a month. However, despite the ability of EF3030 to persist, mutations in NanA significantly reduced numbers of pneumococcal cells in the nose. Attenuation was even more dramatic in the TGR4/NanA– strain where numbers of cells isolated from the nasal wash fell to close to the detectable limit after 14 days.

In the natural setting the pneumococcus co-exists with other bacterial species. Thus NanA's other functions may include altering the function of host proteins and contributing to the long term stability of carriage. NanA may also enhance pneumococci's ability to compete with other oral microbes including N. meningitidis and H. influenzae or by making host glycoproteins available as a carbon source.

Although the major result of these studies has been the demonstration that NanA expression was required for optimal carriage in mice, these data also demonstrated that pneumococci lacking NanA were found in much lower numbers in the olfactory bulbs. It is difficult at this point to know if an active NanA is important for survival of S. pneumoniae in CNS tissues. Although the numbers of NanA mutants recovered from these tissues are much less than the parental strain, their very presence in neuronal tissues argues an additional virulence effect of NanA once the pneumococci enter the brain. The decreased level of neuraminidase-mutants in the OB is very likely to be the result of diminished carriage. This finding underscores the principle that carriage is a prerequisite for more invasive diseases and that interventions capable of reducing carriage, such as immunization with NanA, will offer protection against pneumoniae, meningitis, otitis-media and sepsis.

Of the known sequences for nanA, the TIGR sequence is the only one that does not contain a surface anchor. In this strain, a frame shift results in truncation of the molecule prior to the LPETG (SEQ ID NO: 13) motif (Tettelin et al. 2001 Science 293:498-506). For most strains a significant portion of the NanA is expected to be covalently attached to the cell wall by sortase (azmanian et al. 1999 Science 285:760-63) where it has been detected in electron micrographs (Camara et al. Infect. Immun. 62:3688-95). In these studies, TIGR4 as well as EF3030 exhibited NanA dependent carriage and presence in the olfactory bulbs. From studies of the localization of NanA activity in the supernatant or bacterial pellet, it was shown that, unlike TIGR4, the NanA activity of EF3030 is cell associated. Thus, NanA can facilitate colonization whether it is surface bound or whether it is secreted.

Example 3

The Role of Gangliosides in S. pneumoniae Pathogenesis

Purified neuraminidase, NanA (Calbiochem), is administered at 1, 10 and 50 µg in 10 µl PBS nasally 15, 30 and 60 minutes prior to isolating the ON/E. The tissues are fixed in 4% paraformaldehyde, and paraffin sections made. GM1 is stained for using biotinylated-CT-B followed by Streptavidin-FITC and the intensity of staining is analyzed. The section is also stained by asialo-GM1-specific Abs conjugated to rodamine to confirm a decrease of GM1 staining coincident with increase of asialo-GM1 staining in these tissues. Parallel groups of mice undergoing the same treatment are analyzed for colonization by S. pneumoniae strain TIGR4 and EF3030 at days 1 and 4, to assure that neuraminidase treatment resulted in elevated levels of nasal colonization. Mice are given a high dose of strain EF3030 ($1 \times 10^8$ CFU) nasally and the ON/E is isolated at the following intervals: 1, 3, 6, and 12 hrs, 1 and 4 days after nasal challenge. The ON/E is stained as outlined above and analyzed for GM1 and asialo-GM1 expression. If decreased GM1 and elevated asialo-GM1 expression are observed in the nasal tissues, then the NanA- and NanB-deficient strains are also tested since they would be expected not to alter GM1 expression in the nasal tract. The removal of sialic acid residues exposes the subterminal disaccharide, β-D-galactopyranosyl-(1-3)N-acetyl-D-galactosamine, which represents an immunodominant group of the Thompson-Friedenreich antigen, for which PNA has high affinity. Thus, changes in the PNA-binding sites in the ON/E is another measure of neuraminidase activity. Frozen sections made from these tissues are readily stained with PNA-FITC or PNA-HRP (Medac, Hamburg, Germany) to determine if an increase in PNA-binding sites occurs based on microscopy (Black et al., (2000) Pediatr. Infect. Dis J. 19: 187-195; Klein et al. (1978) Klin. Wochenschr. 56: 761-765, which are incorporated herein by reference in their entirety for the methods taught therein).

The GM1 site is specifically blocked prior to nasal administration of strain TIGR4 or EF3030. This is approached in three ways by using: 1) CT-B versus a non-ganglioside control protein e.g. ovalbumin, 2) Abs to GM1 (Calbiochem) versus normal rabbit imunoglobulins, or 3) GM1-specific peptides synthesized in the UAB Protein Analysis and Peptide Synthesis Core Facility. The inhibition with the GM1-specific peptide is the best approach since CT-B and possibly Abs to GM1 is expected to cause concomitant inflammation. In these experiments the ON/E and OBs are analyzed 1 and 4 days after application for pneumococcal CFU. An alternative approach of blocking GM1 is the use of a GM1-binding peptide that was discovered by use of a phage-display pentadecapeptide library selecting for GM1-binding peptides. This GM1-binding peptide VWRLLAPPFSNRLLP (SEQ ID NO:5) has high affinity ($10^{10}$ $M^{-1}$) for GM1 and an $IC_{50}$ of 1.0 μM. Matsubura et al., (1999) FEBS Letters 456: 253-256. A peptide of the same length and composed of the same amino acids in a randomly selected sequence is used as control. The GM1-binding ability of both peptides is confirmed by ELISA prior to use in vivo. Initially, 100 μg of these two peptides is administered nasally in 10 μl Ringer's solution or PBS, 10 minutes prior to applying $3\times10^6$ CFU of strain EF3030. The ON/E is analyzed for CFU on days 1 and 4 after application for numbers of CFU relative to untreated CBA/N mice.

Blocking experiments are performed with PAF (Biomol Research Laboratories, Inc. Plymouth meeting, Pa.) and the PAF-R antagonist octylonium bromide (Biomol). This compound binds with high affinity to the PAF-R. Each ganglioside is tested individually. Besides mixed gangliosides, asialo-GM1, GM1, GD1a, GD1b, GT1 (Calbiochem) and the GM3 (Sigma) are tested for their ability to inhibit nasal colonization as assessed on day 1 and 4 after challenge. Various gangliosides are able to block this process. The GM3 ganglioside functions as a negative control since it lacks the published C-polysaccharide binding motif. Based on the data presented on colonization with EF3030 following ganglioside preincubation, mixed gangliosides are more effective than asialo-GM1 at blocking colonization. This indicates that other gangliosides besides asialo-GM1 are involved in the process of pneumococcal colonization of the nasal tract, lungs and brain. These ganglioside inhibition studies focus on the TIGR4 strain and its neuraminidase mutants. Short term in vitro incubation with the TIGR4 strain on ganglioside-coated ELISA plates demonstrated attachment of the TIGR4 strain to the asialo-GM1. Enterotoxins provide another means of differentially blocking pneumococci-ganglioside interactions in the nasal tract. Both CT and LTh-1 are both serogroup I heat-labile enterotoxins (Pickett et al., (1986) J. Bacteriol 165: 348-352) and display similar, although slightly different, ganglioside binding specificities. Fukuta et al., (1988) Infect Immun. 56: 1748-1753. CT (List Biological Laboratories, Inc., Campbell, Calif.) binds to GM1 and to a lesser extent to GD1b. LTh-1 displays preferential binding to GM1 and GD1b and binds weakly to GM2 and asialo-GM1. Fukuta et al., (1988) Infect Immun. 56: 1748-1753. If GM1 is the main ganglioside interacting with *S. pneumoniae*, the use of LTh-1 would not only block the GM1 ganglioside but might also block asialo-GM1, which could represent a natural low frequency binding site not requiring neuraminidase activity. The heat-labile enterotoxins from serogroup II display different ganglioside binding specificities, in particular the heat-labile enterotoxin LT-IIb. This toxin binds to GD1a and to a lesser extent to GT1b and showed no affinity for GM1. Fukuta et al., (1988) Infect Immun. 56: 1748-1753. The LT-IIa binds with high affinity to GD1b and with a lower affinity to GM1, GT1b, GQ1b, GD2, GD1a, and GM2. Fukuta et al., (1988) Infect Immun. 56:1748-1753. The LT-II toxins have been kindly provided by Dr. T. D. Connell. To optimize the nasal dose and the optimal time period to observe inhibition of pneumococcal attachment to ON/E, a dose response study (1.0 or 10 μg) is initially performed on a selected enterotoxin, which is given during nasal application of *S. pneumoniae*. If inhibition of nasal colonization is observed on day 4 the observations are extended to day 11 during which enterotoxin is given every other day. The CFU in ON/E and OBs of CBA/N mice are measured.

Example 4

The Role of C-Polysaccharide-Specific Antibodies in Pneumococcal Pathogenesis Pneumococcal C-polysaccharide, also known as teichoic acid, is structurally identical to the pneumococcal F-antigen, also known as lipoteichoic acid. Fischer et al. (1993) Eur. J. Biochem 215: 851-857. This is a unique feature of *S. pneumoniae* among gram-positive bacteria. The immunodominant determinants on these molecules are the phosphorylcholine (PC) residues and Abs to PC are protective against i.p. or nasal pneumococcal challenge. Briles et al., (1984) Eur. J. Immunol. 14: 1027-1030; Briles et al., (1981) Nature 294: 88-90; Yother et al., (1982) Infect. Immun. 36:184-188; Briles et al., (1984) J. Mol. Cell. Immunol. 1:305-309. Thus, the role of PC-specific Abs, either obtained by passive transfer or active nasal immunization, is explored. For passive transfer of protective PC-specific Abs, i.e., T15 idiotypic monoclonal Abs (mAbs) of both the IgG3 (59.6C5) and IgM (22.1A4) isotypes are used. Briles et al., (1981) Nature 294: 88-90. The T15 idiotype has been shown to be more protective than the M603 or M511 idiotypes against pneumococcal infection in mice (Briles et al., (1984) Eur. J. Immunol. 14: 1027-1030), presumably by more efficiently binding the C-polysaccharide. Passive Ab transfer involves the direct application of T15 Abs (100 μg) with nasally applied pneumococci and is compared to i.v. or i.p. administered Abs for reducing nasal colonization. Colonization is monitored over time (day 4, 11, 18) and if no significant difference is observed between the different groups in these experiments mAbs (20 μg) are applied nasally every other day. CBA/N mice, do not produce T15 idiotypic anti-PC Abs. Passive transfer of anti-PC-specific Abs is not expected to induce mucosal IgA or other isotypes of PC-specific Abs in the nasal tract. In order to induce nasal Abs, two different approaches are taken. One is the direct nasal application of the protease treated R36A strain, which is known to induce Ab responses to C-polysaccharide. Although protective immunity of anti-PC Abs has been studied, no data is available on their role at mucosal surfaces such as the nasal tract. The CBA/N mice X-chromosome-linked immunodeficiency results in an inability to generate anti-PC Abs of the T15-idiotype. To determine the importance of this inability CBA/N mice are compared to their wildtype counterpart the CBA/J mice (Jackson Laboratories). Immunization with strain R36A for induction of anti-PC Abs involves proteolytic removal of surface protein. Krause (1970) Adv. Immunol. 12: 1-56. The alternative approach for nasal immunization is coupling of PC to the protein keyhole limpet hemocyanin (KLH) as previously described (Krause (1970) Adv. Immunol 12: 1-56; Chesebro and Metzger (1972) Biochemistry 11: 766-771, which are incorporated herein by reference for the methods taught therein). Nasal immunization with PC-KLH is performed with the mucosal adjuvant CT to optimize mucosal immune responses. The mice are challenged 2-3 weeks after the last immunization to prevent effects of CT on colonization. Three nasal immunizations are performed at one week intervals. The serum Ab titers are monitored using a C-polysaccharide and PC-specific ELISA as routinely performed by those skilled in the art. For the PC-specific ELISA, PC is coupled to BSA as described previously (Chesebro and Metzger (1972) Biochemistry 11: 766-771, which is incorporated herein by reference for the methods taught therein). In addition to serum, the Ab titers in nasal washes, saliva, and bronchial lavages are measured. These analyses include IgA, IgM, IgG, and IgG-subclass distribution in both mucosal secretions and serum. The protocol that induces the most optimal mucosal Ab titers is used to perform mucosal challenge studies with the TIGR4 strain, which is administered nasally at ~5×10$^6$ CFU to mice after which colonization is monitored on day 4 and 11. In the immunization studies normal, fully immunocompetent mice (CBA/J strain) as well as CBA/N mice are used as in previous studies. Wallick et al., (1983) J. Immunol. 130: 2871-2875.

Example 5

The Role of Neuraminidase-Specific Antibodies in *S. pneumoniae* Pathogenesis

To nasally immunize the mice prior to nasal challenge commercially available *S. pneumoniae*-derived neuraminidase is used (Calbiochem). However, the NanA gene is cloned and expressed in *E. coli* using a histidine-tag containing expression vector (Invitrogen) in order to obtain sufficient amounts of protein for the proposed studies. Nasal immunization of 3.4% formaldehyde-treated neuraminidase is compared versus-untreated neuraminidase in the presence or absence of CT in order to optimize the mucosal immune responses. These immunizations are performed in both CBA/N and CBA/J mice. Three nasal immunizations are given one week apart during which serum and saliva Abs titers are monitored by ELISA. The immune mice are challenged with the TIGR4 strain and the colonization of ON/E, OB, brain, blood, spleen, and lungs is compared on days 4 and 11. To block host interaction, both neuraminidase and C-polysaccharide-specific Abs are induced simultaneously. A combined regimen of nasal immunization with neuraminidase and passive immune protection by transfer of T15 idiotypic mAbs is used.

Example 6

The Efficacy of Neuraminidase-PC Conjugate to Protect Against Nasal Challenge with *S. pneumoniae*

Mice are immunized with neuraminidase and PC-KLH in combination with CT as nasal adjuvant to assess enhancement of protection and decrease nasal colonization by the EF3030 and TIGR4 strains on day 11 compared to each antigen used alone. In addition, Ab titers in nasal washes, saliva, and serum are analyzed as indicated above to correlate immune parameters with degree of protection to pneumococci in the nasal tract. To generate a more optimal immune response phosphocholine is directly coupled to neuraminidase. This construct is tested for immunogenicity when delivered with or without CT as adjuvant after nasal and systemic immunization in both CBA/N and CBA/J mice. The Ab titers in nasal washes, saliva, and plasma are measured by ELISA. Challenge studies are performed with 10$^7$ CFU of strains EF3030 or 10$^6$ TIGR4. The mice are sacrificed on day 11 after challenge and analyzed for CFUs observed in blood, nasal washes, ON/E, OB, and brain. Immunization with neuraminidase coupled to PC enhances protection by increasing mucosal and systemic Ab levels to these two virulence components. The antigen-specific IgG subclass distribution are altered by using other mucosal adjuvants. CT generates a Th2−, LT a mixed Th2/Th1−, and CpG motifs such as the DNA oligonucleotide (ODN) 1826 a Th1-type response with associated changes in IgG subclass distribution. Different adjuvants further enhance the ability of neuraminidase-C-polysaccharide-specific immunity to protect against nasal colonization by *S. pneumoniae* and lead to the formulation of new pneumococcal vaccine approaches.

Example 7

Inhibition of Nasal Colonization of *S. pneumoniae* by Anti-Phosphocholine-Specific Monoclonal Antibodies after Nasal Challenge A total of 1×10$^6$ CFU of the TIGR4 strain were incubated with 5 μg of anti-phosphocholine monoclonal antibodies of either the IgG3 subclass or IgM isotype. A total of 5 μl was administered per nare. Indicated are the CFUs in 500 ml nasal wash respectively 9 and 12 hours after application. A significant over 80% decrease was observed for both monoclonal antibodies. Indicated are the mean+SD of five mice per group. The data are shown in FIG. 10.

Example 8

Neuronal Damage and Inflammation after Nasal *S. pneumoniae* Application

The ON/E, OB, and brain are isolated from treated mice at days 1, 3, 7, and 14 after nasal application of *S. pneumoniae* strain EF3030 and analyzed histologically for inflammatory responses. The D39 or TIGR4 strains are compared to their nanA mutant strains for their ability to generate inflammatory responses. At sacrifice, the mice are perfused with PBS at 25° C., followed by perfusion with 100 ml of Zamboni's fixative (4% paraformaldehyde, 15% picric acid in 0.1 M phosphate buffer. The OB and ON/E are removed and then placed in fresh 4% paraformaldehyde (PFA) at 4° C. overnight. The tissue is then transferred to a 30% sucrose solution at 4° C. for 48 hr to cryoprotect it prior to sectioning. The tissues are then frozen in OCT and sections (6 μm) are placed on previously coated microscope slides (10% BSA in saline). Initially, hematoxylin and eosin (H&E) staining are performed to detect any inflammatory cell infitrates in the OB, trigeminal ganglia and ON/E during this time period. In order to assess neuronal damage, nerve growth factor β1 (NGF-β1) is stained for. NGF-β1 is produced after neuronal damage and functions to prevent apoptosis and to stimulate new growth of nerve cells. Trigeminal ganglia and OB sections are stained with a biotinylated rabbit anti-human NGF-β1 Ab at a concentration 0.2 µg/ml. The Ab-stained sections are incubated at 4° C. overnight. The sides are rinsed with PBS and then reacted with avidin-biotin-complex (ABC) Vectastain (Vector Laboratories, Burlingame, Calif.) for 30 min at 25° C. The tissue is rinsed 3 times with PBS and then reacted with diaminobenzidene (DAB) for 5-10 min as previously reported. The slides are rinsed 3 more times and sections counterstained with C.S. hematoxylin for 30 sec. After washing in $H_2O$, the slides are dehydrated in 100% alcohol and xylene. An increase in NGF-β1 provides an indication of the degree of damage in neuronal tissues. Another indicator for neuronal involvement is the activation of microglia. Activated microglia display an amoeboid, spherical shape while resting cells (in $G_0/G_1$) have an arborized, ramified appearance. This change upon activation allows one to distinguish resting and activated microglia. For microglia, F4/80 antibody or anti-MAC-1 (MI/70) are used to address the activation state after *S. pneumoniae* challenge. In addition to neuronal damage and microglia activation, the induction of apoptosis in OB is assessed. To this end, the induction of active Caspase 3, an Asp-Glu-Val-Asp specific protease, is analyzed because it is important in the initiation of apoptotic pathways. An Ab specific for active Caspase 3 (Cell Signaling Technology, Inc., Beverly, Mass.) can be used in immunohistochemistry for detection of apoptosis. If Caspase 3 activity is detected in neuronal tissues by immunohistochemistry, activity is quantified using a Caspase-3 Assay kit (Molecular probes, Eugene, Oreg.) based on a fluorescent signal induced after proteolysis of the substrate.

Example 9

Ability of *S. pneumoniae* to Target Olfactory Bulbs by Retrograde Axonal Transport First, accumulation of pneumococci in the neuronal tissues, OB and brain, of treated mice following nasal and i.v. inoculation is assessed. Following i.v. inoculation, any pneumococci in the neuronal tissues has entered through the blood. Tissues at 1, 4, 11 and 18 days following nasal challenge are collected. In that case the numbers of bacteria per gram of brain and OB should be similar at all time points post injection. In contrast, for bacteria entering through the nasal tract following intranasal inoculation, an accumulation in the OB (expressed per weight of tissue) precedes and in general remains ahead the accumulation observed in the brain.

Second, in vivo imaging of pneumococci after nasal application is performed. Technetium-99 (Tc-99m)-labeled TIGR4, stable opaque and transparent variants, EF3030, and TIGR4 mutants lacking nanA and/or nanB are used to visualize their presence in mice using gamma camera imaging as previously performed with adenovirus using a strategy originally described by Waibel et al. (1999) Nature Biotechnol. 17:897-901. This allows imaging for approximately the first 24 hrs following nasal application due to the short half live (6 hrs) of this isotope and allows analysis of the early events taking place in the nasal tract. For long term imaging of the pneumococci, a luciferase- or GFP-expressing pneumococcal EF3030 (or TIGR4) strain are used to visualize the bioluminescence in vivo. A luciferase-expressing pneumococci strain EF3030, commercially available from the Xenogen corporation (Alameda, Calif.), is used. Successful in vivo imaging with this pneumococcal strain has been previously reported. The mice are imaged using a bioluminescence imaging system (IVIS system, Xenogen, Inc.) to detect luciferase expression. Images are collected on mice oriented in the same position and always at 10 min after i.p. injection of 2.5 mg luciferin. During imaging the mice are maintained under enflurane anesthesia at 37° C. Imaging is performed several times on each mouse, beginning at 2 days to 18 days after nasal challenge with luciferase-expressing pneumococci. Image acquisition times for imaging are in the range of 20 sec to 10 min. Data acquisition software insures that no pixels are saturated during image collection. Light emission from the regions of interest (relative photons/sec) are quantitated using software provided by Xenogen. The intensity of light emission is represented with a pseudocolor scaling of the bioluminescent images. The bioluminescent images are typically overplayed on black and white photographs of the mice that are collected at the same time. This in vivo imaging focuses on analyzing the ability of pneumococci to enter the OBs from the nasal tract. This bioluminescence studies extend to the nanA TIGR4 mutant after successful transfer of the luciferase gene.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

REFERENCES

Amsbaugh, D. F., Hansen, C. T., Prescott, B., Stashak, P. W., Barthold, D. R., and Baker, P. J. (1972) Genetic control of the antibody response to type III pneumococcal polysaccharide in mice. I. Evidence that an X-linked gene plays a decisive role in determining responsiveness. J. Exp. Med. 136: 931-949.

Anon. 2000. Surveillance of preliminary reports from 18 countries and the USA. CDSC European Bacterial Meningitis Surveillance Project. PHLS, London.

Avery, O. T., C. M. MacLeod, and M. McCarty. 1979. Studies on the chemical nature of the substance inducing transformation of pneumococcal types. Induction of transformation by a desoxyribonucleic acid fraction isolated from pneumococcus type III. J. Exp. Med 149:297-326.

Balachandran, P., Brooks-Walters, A., Virolainen-Julkunen, A., Hollingshead, and Briles, D. E. 2002. Role of pneumococcal surface protein C in nasopharyngeal carriage and pneumonia and its ability to elicit protection against carriage of *Streptococcus pneumoniae*. Infect. Immun. 70: 2526-2534.

Bennett, S. A. L., Chen, J., Pappas, B. A., Roberts, D. C. S. and Tenniswood, M. 1998. Alterations in platelet activating factor receptor expression associated with neuronal apoptosis in an in vivo model of excitotoxicity. Cell Death Differ. 5: 867-875.

Berning, A. K., Eicher, E. M., Paul, W. E., and Scher, I. (1980) J. Immunol. 124:1875-1877.

Berry, A. M., and J. Paton, C. 2000. Additive attenuation of virulence of *Streptococcus pneumoniae* by mutation of the genes encoding pneumolysin and other putative pneumococcal virulence proteins. Infect. Immun. 68:133-140.

Berry, A. M., Lock, R. A., and Paton, J. C. 1996. Cloning and characterization of nanB, a second from *S. pneumoniae* neuraminidase gene, and purification of the NanB enzyme from recombinant *Escherichia coli*. J. Bacteriol. 178: 4854-4860.

Berry, A. M., J. C. Paton, E. M. Glare, D. Hansman, and D. E. A. Catcheside. 1988 Cloning and expression of the pneumococcal neuraminidase gene in *Escherichia coli*. Gene 71:299-305.

Black, S., Shinefield, H., Fireman, B., Lewis, E., Ray, P., Hansen, J. R., Elvin, L., Ensor, K. M., Hackell, J., Siber, G., Malinoski, F., Madore, D., Chang, I., Kohberger, R., Watson, W., Austrian, R., and Edwards, K. 2000. Efficacy, safety and immunogenicity of heptavalent pneumococcal conjugate vaccine in children. Pediatr. Infect. Dis. J. 19: 187-195.

Brewer, C., Bonin, F., Bullock, P., Nault, M. C., Morin, J., Imbeault, S., Shen, T. Y., Franks, D. J. and Bennett, S. A. 2002. Platelet activating factor-induced apoptosis is inhibited by ectopic expression of the platelet activating factor G-protein coupled receptor. J. NeuroChem. 82: 1502-1511.

Briles, D. E., S. K. Hollingshead, J. C. Paton, E. W. Ades, L. Novak, F. W. van Ginkel, and W. H. J. Benjamin. 2003. Immunizations with pneumococcal surface protein A and pneumolysin are protective against pneumonia in a murine model of pulmonary infection with *Streptococcus pneumoniae*. J Infect Dis 188:339-348.

Briles, D. E., Chaflin, J. L., Schroer, K., and Forman, C. 1981. Mouse IgG3 antibodies are highly protective against infection against *Streptococcus pneumoniae*. Nature 294: 88-90.

Briles, D. E., Crain, M. J., Gray, B. M., Forman, C., and Yother, J. 1992. Infect. Immun. 60:111-116.

Briles, D. E., Forman, C., Hudak, S., and Claflin, J. L. 1984. The effects of idiotype on the ability of IgG1 anti-phosphorycholine antibodies to protect mice from fatal infection with *Streptococcus pneumoniae*. Eur. J. Immunol. 14: 1027-1030.

Briles, D. E., Forman, C., Hudak, S., and Claflin, J. L. 1984. The effects of subclass on the ability of anti-phosphocholine antibodies to protect mice from fatal infection with *Streptococcus pneumoniae*. J. Mol. Cell. Immunol. 1: 305-309.

Briles, D. E., J. Horowitz, L. S. McDaniel, W. H. Benjamin, Jr., J. L. Claflin, C. L. Booker, G. Scott, and C. Forman. 1986. Genetic control of susceptibility to pneumococcal infection. Curr. Top. Microbiol. Immunol. 124:103-120.

Briles, D. E., M. Nahm, K. Schroer, J. Davie, P. Baker, J. Kearney, and R. Barletta. 1981. Antiphosphocholine antibodies found in normal mouse serum are protective against intravenous infection with type 3 *Streptococcus pneumoniae*. J. Exp. Med. 153:694-705.

Brooks-Walter, A., Briles, D. E., and Hollingshead, S. K. 1999. The PspC gene of *Streptococcus pneumoniae* encodes a polymorphic protein, PspC, which elicits cross-reactive antibodies to PspA and provides immunity to pneumococcal bacteremia. Infect. Immun. 67:6533-6542.

Butler, J. C. and Schuchat, A. 1999. Epidemiology of pneumococcal infections in the elderly. Drugs Aging 15(Suppl. 1):11-19.

Camara, M., G. J. Boulnois, P. W. Andrew, and T. J. Mitchell. 1994. A neuraminidase from *Streptococcus pneumoniae* has the features of a surface proteins. Infect. Immun. 62:3688-95.

Chesebro, B. and Metzger, H. 1972. Affinity labeling of a phosphorylcholine binding mouse myeloma protein. Biochemistry 11:766-771.

Crennell S J, Garman E F, Layer W G, Vimr E R, Taylor G L (1993) Crystal structure of a bacterial sialidase (from *Salmonella typhimurium* LT2) shows the same fold as an influenza virus neuraminidase. Proc Natl Acad Sci USA. 90(21):9852-56.

Fedson, D. S., Scott, J. A. and Scott. G. 1999. The burden of pneumococcal disease among adults in developed and developing countries: what is and is not known [In Process Citation]. Vaccine. 17 Suppl. 1:S11-18.

Fedson, D. S., Shapiro, E. D., LaForce, F. M., Mufson, M. A., Musher, D. M., Spika, J. S., Breiman, R. F. and Broome, C. V. 1994. Pneumococcal vaccine after 15 years of use. Another view. Arch. Intern. Med. 154:2531-2535.

Fischer, W., Behr, T., Hartmann, R., Peter-Katalinic, J., and Egge, H. 1993. Teichoic acid and lipoteichoic acid of *Streptococcus pneumoniae* posses identical chain structure. A reinvestigation of teichoic acid (C polysaccharide). Eur. J. Biochem. 215: 851-857.

Fukuta, S., Magnani, J. L., Twiddy, E. M., Holmes, R. K., and Ginsburg, V. 1988. Comparison of the carbohydrate-binding specificities of cholera toxin and *Escherichia coli* heat-labile enterotoxins LTh-I, LT-IIa, and LT-IIb. Infect. Immun. 56: 1748-1753.

Gerard, N. P., Gerard, C. 1994. Receptor-dependent internalization of platelet-activating factor. J. Immunol. 152: 793-800.

Honda, Z., Nakamura, M., Seyama, Y., Shimizu, T. 1992. Properties of the guinea-pig lung platelet-activating factor receptor encoded by the cloned cDNA. J. Lipid Med. 5: 105-107.

Hoskins, J., W. E. Alborn, Jr., J. Arnold, L. C. Blaszczak, S. Burgett, B. S. DeHoff, S. T. Estrem, L. Fritz, D. J. Fu, W. Fuller, C. Geringer, R. Gilmour, J. S. Glass, H. Khoja, A. R. Kraft, R. E. Lagace, D. J. LeBlanc, L. N. Lee, E. J. Lefkowitz, J. Lu, P. Matsushima, S. M. McAhren, M. McHenney, K. McLeaster, C. W. Mundy, T. I. Nicas, F. H. Norris, M. O'Gara, R. B. Peery, G. T. Robertson, P. Rockey, P. M. Sun, M. E. Winkler, Y. Yang, M. Young-Bellido, G. Zhao, C. A. Zook, R. H. Baltz, S. R. Jaskunas, P. R. Rosteck, Jr., P. L. Skatrud, and J. I. Glass. 2001. Genome of the bacterium *Streptococcus pneumoniae* strain R6. J Bacteriol 183:5709-17.

Hoyer, L. L., A. C. Hamilton, S. M. Steenbergen, and E. R. Vimr. 1992. Cloning, sequencing and distribution of the *Salmonella typhimurium* LT2 sialidase gene, nanH, provides evidence for interspecies gene transfer. Mol Microbiol 6:873-84.

Kelly, R. T., Farmer, S., and Greiff, D. 1967. Neuraminidase activities of clinical isolates of *Diplococcus pneumoniae*. J. Bacteriol. 94: 272-273.

King, S. J., K. R. Hippe, J. M. Gould, D. Bae, S. Peterson, R. T. Cline, C. Fasching, E. N. Janoff, and J. N. Weiser. 2004. Phase variable desialylation of host proteins that bind to *Streptococcus pneumoniae* in vivo and protect the airway. Mol Microbiol 54:159-71.

Klein, P. J., Newman, R. A., Muller, P., Uhlenbruck, G., Schaefer, H. E., Lennartz, K. J., and Fischer, R. 1978. Histochemical methods for the demonstration of Thomsen-Friedenreich antigen in cell suspensions and tissue sections. Klin. Wochenschr. 56: 761-765.

Krause, R. M. 1970. The search for antibodies with molecular uniformity. Adv. Immunol. 12:1-56.

Krivan, H. C., D. D. Roberts, and V. Ginsburg. 1988. Many pulmonary pathogenic bacteria bind specifically to the carbohydrate sequence GalNAc beta 1-4Gal found in some glycolipids. Proc Natl Acad Sci USA 85:6157-61.

LaMarco, K. L., W. F. Diven, and R. H. Glew. 1986. Experimental alteration of chinchilla middle ear mucosae by bacterial neuraminidase. Ann Otol Rhinol Laryngol 95:304-8.

Lock, R. A., J. C. Paton, and D. Hansman. 1988. Purification and immunologic characterization of neuraminidase produced by *Streptococcus pneumoniae*. Microb. Pathog. 4:33-43.

Lock, R. A., Paton, J. C., and Hansman, D. 1988. Comparative efficacy of pneumococcal neuraminidase and pneumolysin as immunogens protective against *Streptococcus pneumoniae*. Microb. Pathog. 5(6): 461-7.

Long, J. P., H. H. Tong, and T. F. DeMaria. 2004. Immunization with native or recombinant *Streptococcus pneumoniae* neuraminidase affords protection in the chinchilla otitis media model. Infect Immun 72:4309-13.

Lysenko, E. S., J. Gould, R. Bals, J. M. Wilson, and J. N. Weiser. (2000) Bacterial phosphorylcholine decreases susceptibility to the antimicrobial peptide LL-37/hCAP18 expressed in the upper respiratory tract. Infect Immun 68: 1664-71.

Madhi, S. A., and K. P. Klugman. 2004. A role for *Streptococcus pneumoniae* in virus-associated pneumonia Nat Med 10:811-3.

Magee, A. and Yother, J. (2001) Requirement for capsule in colonization by *Streptococcus pneumoni*. Infect. Immun. 69: 3755-3761.

Martin, F., Won, W-J. and Kearney, J. F. 1998. Generation of the germline peripheral B cell repertoire: VH81X-□B cells are unable to complete all developmental programs. J. Immunol. 160: 3748-3758.

Mazmanian, S. K., G. Liu, H. Ton-That, and O. Schneewind. 1999. *Staphylococcus aureus* sortase, an enzyme that anchors surface proteins to the cell wall. Science 285:760-63.

Matsubara T., Ishikawa. D., Taki, T., Okahata, Y., and Sato, T. 1999. Selection of ganglioside GM1-binding peptides by using phage library. FEBS Letters 456:253-256.

McCullers, J. A., and K. C. Bartmess. 2003. Role of neuraminidase in lethal synergism between influenza virus and *Streptococcus pneumoniae*. J Infect Dis 187:1000-9.

McDaniel, L. S., W. D. Waltman, B. Gray, and D. E. Briles. 1987. A protective monoclonal antibody that reacts with a novel antigen of pneumococcal teichoic acid. Microb. Pathog. 3:249-260.

Mori, M, Aihara, M., Kume, K., Hamanoue, M., Kohsaka, S. and Shimizu, T. 1996. Predominant expression of platelet-activating factor receptor in rat brain microglia. J. Neurosci. 16:3590-3600.

O'Toole, R. D., Goode, L., and Howe, C. 1971. Neuraminidase activity in bacterial meningitis. J. Clin Invest. 50: 979-985.

Pickett, C. L., Twiddy, E. M., Belisle, B. W., and, Holmes, R. K. 1986. Cloning of genes that encode a new heat-labile enterotoxin of *Escherichia coli*. J. Bacteriol. 165: 348-352.

Potter, M., J. S. Wax, C. T. Hansen, and J. J. Kenny. 1999. BALB/c.CBA/N mice carrying the defective Btk(xid) gene are resistant to pristane-induced plasmacytomagenesis. Int Immunol 11:1059-64.

Quagliarello, V. and Scheld, W. M. 1992. Bacterial menigitis: pathogenesis, pathophysiology, and progress. N. Eng. J. Med. 327: 864-872.

Scanlon, K. L., Diven, W. F., Glew, R. H. 1989. Purification and properties of *Streptococcus pneumoniae* neuraminidase. Enzyme 41: 143-150.

Shakhnovich, E. A., S. J. King, and J. N. Weiser. 2002. Neuraminidase Expressed by *Streptococcus pneumoniae* Desialylates the Lipopolysaccharide of *Neisseria meningitidis* and *Haemophilus influenzae*: a Paradigm for Interbacterial Competition among Pathogens of the Human Respiratory Tract. Infect Immun 70:7161-4.

Stengel, D., Antonucci, M., Arborati, M., Hourton, D., Griglio, S., Chapman, M. J., and Ninio, E. Expression of the PAF receptor in human monocyte-derived macrophages is downregulated by oxidized LDL: relevance to the inflammatory phase of atherogenesis. (1997) Arterioscler. Thromb. Vasc. Biol. 17: 954-962.

Sundberg-Kovamees, M., T. Holme, and A. Sjogren. 1996. Interaction of the C-polysaccharide of *Streptococcus pneumoniae* with the receptor asialo-GM1. Microb Pathog 21:223-34.

Sung, C. K., Li, H., Claverys, J. P., and Morrison, D. A. (2001) An rspL cassette, janus, for gene replacement through negative selection in *Streptococcus pneumoniae*. Appl Environ Microbiol 67: 5190-5196.

Tettelin, H., K. E. Nelson, I. T. Paulsen, J. A. Eisen, T. D. Read, S. Peterson, J. Heidelberg, R. T. DeBoy, D. H. Haft, R. J. Dodson, A. S. Durkin, M. Gwinn, J. F. Kolonay, W. C. Nelson, J. D. Peterson, L. A. Umayam, O. White, S. L. Salzberg, M. R. Lewis, D. Radune, E. Holtzapple, H. Khouri, A. M. Wolf, T. R. Utterback, C. L. Hansen, L. A. McDonald, T. V. Feldblyum, S. Angiuoli, T. Dickinson, E. K Hickey, I. E. Holt, B. J. Loftus, F. Yang, H. O. Smith, J. C. Venter, B. A. Dougherty, D. A. Morrison, S. K. Hollingshead, and C. M. Fraser. 2001. Complete genome sequence of a virulent isolate of *Streptococcus pneumoniae*. Science 293:498-506.

Tong, H. H., Blue, L. E., James, M. A., and DeMaria, T. F. 2000. Evaluation of the virulence of a *Streptococcus pneumoniae* neuraminidase-deficient mutant in nasopharyngeal colonization and development of otitis media in the chinchilla model. Infect. Immun. 68: 921-924.

Tong, H. H., M. James, L Grants, X. Liu, G. Shi, and T. F. DeMaria. 2001. Comparison of structural changes of cell surface carbohydrates in the eustachian tube epithelium of chinchillas infected with a *Streptococcus pneumoniae* neuraminidase-deficient mutant or its isogenic parent strain. Microb Pathog 31:309-17.

Valone, F. H. 1988. Identification of platelet-activating factor receptor in P388D1 murine macrophages. J. Immunol. 140:2389-2394.

van Ginkel, F. W., Jackson, R. J., Yuki, Y., and McGhee, J. R. (2000) J. Immunol. (Cutting Edge) 165: 4778-4782.

Vishniakova, L. A., Reztsova, I. V. 1992. The virulence of *Streptococcus pneumoniae* strains—the causative agents of pneumococcal infection at different sites. Zhurnal Mikrobiologii, Epidemiologii i Immunobiologii. 9-10:26-9.

Waibel, R., Alberto, R., Willuda, J., Finnem, R., Schibli, R., Stichelberger, A., Egli, A., Abram, U., Mach, J. P., Pluckthun, A., and Schubiger, P. A. 1999. Stable one-step technetium-99m labeling of His-tagged recombinant proteins with a novel Tc(I)-carbonyl complex. Nature Biotechnol. 17:897-901.

Wicker, L. S., and I. Scher. 1986. X-linked immune deficiency (xid) of CBA/N mice, p. 86-101, Curr. Top. Microbiol. Immunol., vol. 124.

Wu, H-Y., Nguyen, H. H., and Russell, M. W. (1997a) Nasal lymphoid tissue (NALT) as a mucosal immune inductive site. Scand. J. Immunol. 46: 506-513.

Wu, H.-Y., A. Virolainen, B. Mathews, J. King, M. Russell, and D. E. Briles (1997b) Establishment of a *Streptococcus pneumoniae* nasopharyngeal colonization model in adult mice. Microb. Pathog. 23:127-137.

Yother, J., Forman, C., Gray, B. M., and Briles, D. E. 1982. Protection of mice from infection with *Streptococcus pneumoniae* by anti-phosphocholine antibody. Infect. Immun. 36: 184-188.

Yother, J., G. L. Handsome, and D. E. Briles. 1992. Truncated forms of PspA that are secreted from *Streptococcus pneumoniae* and their use in functional studies and cloning of the pspA gene. J. Bact. 174:610-618.

Yother, J., McDaniel, L. S., and Briles, D. E. 1986. Transformation of encapsulated *Streptococcus pneumoniae*. J. Bacteriology 168:1463-1465.

---

What is claimed is:

1. An isolated detoxified pneumococcal neuraminidase wherein the detoxified pneumococcal neuraminidase comprises an amino acid sequence of a non-detoxified neuraminidase A (NanA) (SEQ ID NO: 15 or SEQ ID NO: 16) with at least one amino acid substitution, wherein the amino acid sequence of the detoxified pneumococcal neuraminidase is at least 80% identical to the non-detoxified neuraminidase, and wherein the detoxified pneumococcal neuraminidase has reduced activity as compared to the non-detoxified neuraminidase and wherein the detoxified pneumococcal neuraminidase is antigenic.

2. A composition comprising the isolated detoxified pneumococcal neuraminidase of claim 1 and a pharmaceutically acceptable carrier.

3. The composition of claim 2, further comprising an adjuvant.

4. A composition comprising the isolated detoxified pneumococcal neuraminidase of claim 1 and a pharmaceutically acceptable carrier, wherein the composition is suitable for administration to a mucosal surface.

5. The composition of claim 4, wherein the composition is a nasal spray.

6. The composition of claim 4, wherein the composition is a nebulizer solution.

7. The composition of claim 4, wherein the composition is an aerosol inhalant.

8. A container comprising the composition of claim 4.

9. The container of claim 8, wherein the container is a nasal sprayer.

10. The container of claim 8, wherein the container is a nebulizer.

11. The container of claim 8, wherein the container is an inhaler.

12. The isolated detoxified pneumococcal neuraminidase of claim 1, wherein the amino acid sequence of the detoxified pneumococcal neuraminidase is at least 90% identical to the non-detoxified neuraminidase.

* * * * *

SEQUENCE LISTING

```
<160> NUMBER OF SEQ ID NOS: 17

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 1
atttctgtaa cagctaccaa cga                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 2
gaattccctg tcttttcaaa gtc                                              23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 3
ccgatacact ctcttcccga                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 4
acagttggtg ctaaggaggc                                                  20

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 5

Val Trp Arg Leu Leu Ala Pro Pro Phe Ser Asn Arg Leu Leu Pro
  1               5                  10                  15

<210> SEQ ID NO 6
<211> LENGTH: 34
```

```
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 6
cgcggatcct catactgggt taggaaagtc gtcg                                34

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 7
ggaattccat atgccgacag cagaactacc taaaggc                             37

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 8
ggaattccat atgctggcaa atgaaactca actttcgggg g                        41

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 9
cgcggatcca tcggctttga ccatcggag                                      29

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 10
ggaattccat atgcgtattc cagcacttct caagacag                            38

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 11
ggaacattac ctcgcaaaag g                                              21

<210> SEQ ID NO 12
<211> LENGTH: 19
<212> TYPE: DNA
```

```
<213> ORGANISM: Artificial Sequence
<220> FEATURE:
<223> OTHER INFORMATION: Description of Artificial Sequence:/note =
      Synthetic Construct

<400> SEQUENCE: 12
tacccgcagg cataacatc                                                    19

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 13

Leu Pro Glu Thr Gly
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:/note =
      Synthetic Construct
<220> FEATURE:
<221> NAME/KEY: VARIANT
<222> LOCATION: 3
<223> OTHER INFORMATION: Xaa = any amino acid.

<400> SEQUENCE: 14

Leu Pro Xaa Thr Gly
 1               5

<210> SEQ ID NO 15
<211> LENGTH: 1035
<212> TYPE: PRT
<213> ORGANISM: S. pneumoniae

<400> SEQUENCE: 15

Met Ser Tyr Phe Arg Asn Arg Asp Ile Asp Ile Glu Arg Asn Ser Met
 1               5                  10                  15

Asn Arg Ser Val Gln Glu Arg Lys Cys Arg Tyr Ser Ile Arg Lys Leu
                20                  25                  30

Ser Val Gly Ala Val Ser Met Ile Val Gly Ala Val Val Phe Gly Thr
            35                  40                  45

Ser Pro Val Leu Ala Gln Glu Gly Ala Ser Glu Gln Pro Leu Ala Asn
        50                  55                  60

Glu Thr Gln Leu Ser Gly Glu Ser Ser Thr Leu Thr Asp Thr Glu Lys
 65                  70                  75                  80

Ser Gln Pro Ser Ser Glu Thr Glu Leu Ser Gly Asn Lys Gln Glu Gln
                85                  90                  95

Glu Arg Lys Asp Lys Gln Glu Glu Lys Ile Pro Arg Asp Tyr Tyr Ala
                100                 105                 110

Arg Asp Leu Glu Asn Val Glu Thr Val Ile Glu Lys Glu Asp Val Glu
            115                 120                 125

Thr Asn Ala Ser Asn Gly Gln Arg Val Asp Leu Ser Ser Glu Leu Asp
        130                 135                 140

Lys Leu Lys Lys Leu Glu Asn Ala Thr Val His Met Glu Phe Lys Pro
145                 150                 155                 160
```

-continued

```
Asp Ala Lys Ala Pro Ala Phe Tyr Asn Leu Phe Ser Val Ser Ser Ala
            165                 170                 175

Thr Lys Lys Asp Glu Tyr Phe Thr Met Ala Val Tyr Asn Asn Thr Ala
        180                 185                 190

Thr Leu Glu Gly Arg Gly Ser Asp Gly Lys Gln Phe Tyr Asn Asn Tyr
    195                 200                 205

Asn Asp Ala Pro Leu Lys Val Lys Pro Gly Gln Trp Asn Ser Val Thr
210                 215                 220

Phe Thr Val Glu Lys Pro Thr Ala Glu Leu Pro Lys Gly Arg Val Arg
225                 230                 235                 240

Leu Tyr Val Asn Gly Val Leu Ser Arg Thr Ser Leu Arg Ser Gly Asn
                245                 250                 255

Phe Ile Lys Asp Met Pro Asp Val Thr His Val Gln Ile Gly Ala Thr
            260                 265                 270

Lys Arg Ala Asn Asn Thr Val Trp Gly Ser Asn Leu Gln Ile Arg Asn
        275                 280                 285

Leu Thr Val Tyr Asn Arg Ala Leu Thr Pro Glu Glu Val Gln Lys Arg
    290                 295                 300

Ser Gln Leu Phe Lys Arg Ser Asp Leu Glu Lys Lys Leu Pro Glu Gly
305                 310                 315                 320

Ala Ala Leu Thr Glu Lys Thr Asp Ile Phe Glu Ser Gly Arg Asn Gly
                325                 330                 335

Lys Pro Asn Lys Asp Gly Ile Lys Ser Tyr Arg Ile Pro Ala Leu Leu
            340                 345                 350

Lys Thr Asp Lys Gly Thr Leu Ile Ala Gly Ala Asp Glu Arg Arg Leu
        355                 360                 365

His Ser Ser Asp Trp Gly Asp Ile Gly Met Val Ile Arg Arg Ser Glu
    370                 375                 380

Asp Asn Gly Lys Thr Trp Gly Asp Arg Val Thr Ile Thr Asn Leu Arg
385                 390                 395                 400

Asp Asn Pro Lys Ala Ser Asp Pro Ser Ile Gly Ser Pro Val Asn Ile
                405                 410                 415

Asp Met Val Leu Val Gln Asp Pro Glu Thr Lys Arg Ile Phe Ser Ile
            420                 425                 430

Tyr Asp Met Phe Pro Glu Gly Lys Gly Ile Phe Gly Met Ser Ser Gln
        435                 440                 445

Lys Glu Glu Ala Tyr Lys Lys Ile Asp Gly Lys Thr Tyr Gln Ile Leu
    450                 455                 460

Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Asp
                485                 490                 495

Pro Val Lys Pro Ala Tyr Ser Asp Lys Gly Asp Leu Tyr Lys Gly Asn
            500                 505                 510

Gln Leu Leu Gly Asn Ile Tyr Phe Thr Thr Asn Lys Thr Ser Pro Phe
        515                 520                 525

Arg Ile Ala Lys Asp Ser Tyr Leu Trp Met Ser Tyr Ser Asp Asp Asp
    530                 535                 540

Gly Lys Thr Trp Ser Ala Pro Gln Asp Ile Thr Pro Met Val Lys Ala
545                 550                 555                 560

Asp Trp Met Lys Phe Leu Gly Val Gly Pro Gly Thr Gly Ile Val Leu
                565                 570                 575

Arg Asn Gly Pro His Lys Gly Arg Ile Leu Ile Pro Val Tyr Thr Thr
```

```
                580             585             590
Asn Asn Val Ser His Leu Asn Gly Ser Gln Ser Arg Ile Ile Tyr
            595             600             605

Ser Asp Asp His Gly Lys Thr Trp His Ala Gly Glu Ala Val Asn Asp
610             615             620

Asn Arg Gln Val Asp Gly Gln Lys Ile His Ser Ser Thr Met Asn Asn
625             630             635             640

Arg Arg Ala Gln Asn Thr Glu Ser Thr Val Val Gln Leu Asn Asn Gly
                645             650             655

Asp Val Lys Leu Phe Met Arg Gly Leu Thr Gly Asp Leu Gln Val Ala
            660             665             670

Thr Ser Lys Asp Gly Gly Val Thr Trp Glu Lys Asp Ile Lys Arg Tyr
            675             680             685

Pro Gln Val Lys Asp Val Tyr Val Gln Met Ser Ala Ile His Thr Met
            690             695             700

His Glu Gly Lys Glu Tyr Ile Ile Leu Ser Asn Ala Gly Gly Pro Lys
705             710             715             720

Arg Glu Asn Gly Met Val His Leu Ala Arg Val Glu Glu Asn Gly Glu
                725             730             735

Leu Thr Trp Leu Lys His Asn Pro Ile Gln Lys Gly Glu Phe Ala Tyr
            740             745             750

Asn Ser Leu Gln Glu Leu Gly Asn Gly Glu Tyr Gly Ile Leu Tyr Glu
            755             760             765

His Thr Glu Lys Gly Gln Asn Ala Tyr Thr Leu Ser Phe Arg Lys Phe
            770             775             780

Asn Trp Asp Phe Leu Ser Lys Asp Leu Ile Ser Pro Thr Glu Ala Lys
785             790             795             800

Val Lys Arg Thr Arg Glu Met Gly Lys Gly Val Ile Gly Leu Glu Phe
                805             810             815

Asp Ser Glu Val Leu Val Asn Lys Ala Pro Thr Leu Gln Leu Ala Asn
            820             825             830

Gly Lys Thr Ala Arg Phe Met Thr Gln Tyr Asp Thr Lys Thr Leu Leu
            835             840             845

Phe Thr Val Asp Ser Glu Asp Met Gly Gln Lys Val Thr Gly Leu Ala
850             855             860

Glu Gly Ala Ile Glu Ser Met His Asn Leu Pro Val Ser Val Ala Gly
865             870             875             880

Thr Lys Leu Ser Asn Gly Met Asn Gly Ser Glu Ala Ala Val His Glu
                885             890             895

Val Pro Glu Tyr Thr Gly Pro Leu Gly Thr Ser Gly Glu Glu Pro Ala
            900             905             910

Pro Thr Val Glu Lys Pro Glu Tyr Thr Gly Pro Leu Gly Thr Ser Gly
            915             920             925

Glu Glu Pro Ala Pro Thr Val Glu Lys Pro Glu Tyr Thr Gly Pro Leu
930             935             940

Gly Thr Ala Gly Glu Glu Ala Ala Pro Thr Val Glu Lys Pro Glu Phe
945             950             955             960

Thr Gly Gly Val Asn Gly Thr Glu Pro Ala Val His Glu Ile Ala Glu
                965             970             975

Tyr Lys Gly Ser Asp Ser Leu Val Thr Leu Thr Lys Glu Asp Tyr
            980             985             990

Thr Tyr Lys Ala Pro Leu Ala Gln  Gln Ala Leu Pro Glu Thr Gly Asn
            995             1000            1005
```

```
Lys Glu Ser Asp Leu Leu Ala Ser Leu Gly Leu Thr Ala Phe Phe Leu
        1010                1015                1020
Gly Leu Phe Thr Leu Gly Lys Lys Arg Glu Gln
1025                1030                1035
```

<210> SEQ ID NO 16
<211> LENGTH: 962
<212> TYPE: PRT
<213> ORGANISM: S. pneumoniae

<400> SEQUENCE: 16

```
Met Asn Arg Ser Val Gln Glu Arg Lys Cys Arg Tyr Ser Ile Arg Lys
  1               5                  10                  15
Leu Ser Val Gly Ala Val Ser Met Ile Val Gly Ala Val Val Asn Gly
             20                  25                  30
Thr Ser Pro Val Leu Ala Gln Glu Gly Ala Ser Glu Gln Pro Leu Ala
         35                  40                  45
Asn Glu Thr Gln Leu Ser Gly Glu Ser Ser Thr Leu Thr Asp Thr Glu
 50                  55                  60
Lys Ser Gln Pro Ser Ser Glu Thr Glu Leu Ser Gly Asn Lys Gln Glu
 65                  70                  75                  80
Gln Glu Arg Lys Asp Lys Gln Glu Lys Ile Pro Arg Asp Tyr Tyr
                 85                  90                  95
Ala Arg Asp Leu Glu Asn Val Glu Thr Val Ile Glu Lys Glu Asp Val
            100                 105                 110
Glu Thr Asn Ala Ser Asn Gly Gln Arg Val Asp Leu Ser Ser Glu Leu
        115                 120                 125
Asp Lys Leu Lys Lys Leu Glu Asn Ala Thr Val His Met Glu Asn Lys
130                 135                 140
Pro Asp Ala Lys Ala Pro Ala Phe Tyr Asn Leu Asn Ser Val Ser Ser
145                 150                 155                 160
Ala Thr Lys Lys Asp Glu Tyr Phe Thr Met Ala Val Tyr Asn Asn Thr
                165                 170                 175
Ala Thr Leu Glu Gly Arg Gly Ser Asp Gly Lys Gln Asn Tyr Asn Asn
            180                 185                 190
Tyr Asn Asp Ala Pro Leu Lys Val Lys Pro Gly Gln Trp Asn Ser Val
        195                 200                 205
Thr Phe Thr Val Glu Lys Pro Thr Ala Glu Leu Pro Lys Gly Arg Val
210                 215                 220
Arg Leu Tyr Val Asn Gly Val Leu Ser Arg Thr Ser Leu Arg Ser Gly
225                 230                 235                 240
Asn Phe Ile Lys Asp Met Pro Asp Val Thr His Val Gln Ile Gly Ala
                245                 250                 255
Thr Lys Arg Ala Asn Asn Thr Val Trp Gly Ser Asn Leu Gln Ile Arg
            260                 265                 270
Asn Leu Thr Val Tyr Asn Arg Ala Leu Thr Pro Glu Glu Val Gln Lys
        275                 280                 285
Arg Ser Gln Leu Asn Lys Arg Ser Asp Leu Glu Lys Lys Leu Pro Glu
290                 295                 300
Gly Ala Ala Leu Thr Glu Lys Thr Asp Ile Phe Glu Ser Gly Arg Asn
305                 310                 315                 320
Gly Asn Pro Asn Lys Asp Gly Ile Lys Ser Tyr Arg Ile Pro Ala Leu
                325                 330                 335
Leu Lys Thr Asp Lys Gly Thr Leu Ile Ala Gly Ala Asp Glu Arg Arg
```

-continued

```
                340                 345                 350
Leu His Ser Ser Asp Trp Gly Asp Ile Gly Met Val Ile Arg Arg Ser
            355                 360                 365

Glu Asp Asn Gly Lys Thr Trp Gly Asp Arg Val Thr Ile Thr Asn Leu
        370                 375                 380

Arg Asp Asn Pro Lys Ala Ser Asp Pro Ser Ile Gly Ser Pro Val Asn
385                 390                 395                 400

Ile Asp Met Val Leu Val Gln Asp Pro Glu Thr Lys Arg Ile Asn Ser
                405                 410                 415

Ile Tyr Asp Met Phe Pro Glu Gly Lys Gly Ile Asn Gly Met Ser Ser
            420                 425                 430

Gln Lys Glu Glu Ala Tyr Lys Lys Ile Asp Gly Lys Thr Tyr Gln Ile
        435                 440                 445

Leu Tyr Arg Glu Gly Lys Gly Ala Tyr Thr Ile Arg Glu Asn Gly
        450                 455                 460

Thr Val Tyr Thr Pro Asp Gly Lys Ala Thr Asp Tyr Arg Val Val Val
465                 470                 475                 480

Asp Pro Val Lys Pro Ala Tyr Ser Asp Lys Gly Asp Leu Tyr Lys Gly
                485                 490                 495

Asp Gln Leu Leu Gly Asn Ile Tyr Phe Thr Thr Asn Lys Thr Ser Pro
            500                 505                 510

Asn Arg Ile Ala Lys Asp Ser Tyr Leu Trp Met Ser Tyr Ser Asp Asp
        515                 520                 525

Asp Gly Lys Thr Trp Ser Ala Pro Gln Asp Ile Thr Pro Met Val Lys
        530                 535                 540

Ala Asp Trp Met Lys Phe Leu Gly Val Gly Pro Gly Thr Gly Ile Val
545                 550                 555                 560

Leu Arg Asn Gly Pro His Lys Gly Arg Ile Leu Ile Pro Val Tyr Thr
                565                 570                 575

Thr Asn Asn Val Ser His Leu Asp Gly Ser Gln Ser Ser Arg Val Ile
            580                 585                 590

Tyr Ser Asp Asp His Gly Lys Thr Trp His Ala Gly Glu Ala Val Asn
        595                 600                 605

Asp Asn Arg Gln Val Asp Gly Gln Lys Ile His Ser Ser Thr Met Asn
        610                 615                 620

Asn Arg Arg Ala Gln Asn Thr Glu Ser Thr Val Val Gln Leu Asn Asn
625                 630                 635                 640

Gly Asp Val Lys Leu Asn Met Arg Gly Leu Thr Gly Asp Leu Gln Val
                645                 650                 655

Ala Thr Ser Lys Asp Gly Gly Val Thr Trp Glu Lys Asp Ile Lys Arg
            660                 665                 670

Tyr Pro Gln Val Lys Asp Val Tyr Val Gln Met Ser Ala Ile His Thr
        675                 680                 685

Met His Glu Gly Lys Glu Tyr Ile Ile Leu Ser Asn Ala Gly Gly Pro
        690                 695                 700

Lys Arg Glu Asn Gly Met Val His Leu Ala Arg Val Glu Glu Asn Gly
705                 710                 715                 720

Glu Leu Thr Trp Leu Lys His Asn Pro Ile Gln Lys Gly Glu Asn Ala
                725                 730                 735

Tyr Asn Ser Leu Gln Glu Leu Gly Asn Gly Glu Tyr Gly Ile Leu Tyr
            740                 745                 750

Glu His Thr Glu Lys Gly Gln Asn Ala Tyr Thr Leu Ser Asn Arg Lys
        755                 760                 765
```

```
Asn Asn Trp Glu Asn Leu Ser Lys Asn Leu Ile Ser Pro Thr Glu Ala
        770                 775                 780

Asn Asn Arg Asp Gly Gln Arg Asp Gly Gln Arg Ser Tyr Trp Leu
785                 790                 795                 800

Gly Val Arg Leu Arg Ser Ile Gly Gln Gln Gly Ser Asn Pro Ser Ile
                805                 810                 815

Gly Lys Trp Asn Asn Ser Asp Asn Pro Asn Pro Val Asn Asn Gln Asp
                820                 825                 830

Leu Val Val Cys Ser Arg Asn Gly Arg Tyr Arg Thr Gly Asn Tyr Trp
                835                 840                 845

Tyr Ser Asn Arg Lys His Arg Lys Tyr Ala Asn Ser Ser Cys Lys Ser
        850                 855                 860

Ser Arg Cys Gln Ser Ser Trp Arg Ser Lys Trp Asn Gln Ser Ser Gly
865                 870                 875                 880

Ala Asn Ser Ser Arg Ile Tyr Arg Gly Ser Asn Trp Tyr Arg Ala Ser
                885                 890                 895

Cys Ser Asn Asn Arg Arg Val Asn Gly Ile Asn Phe Ala Cys Asn Ser
                900                 905                 910

Tyr Tyr Lys Lys Arg Leu Tyr Leu Gln Ser Ser Cys Ser Ala Gly
            915                 920                 925

Thr Ser Asn Asn Arg Lys Gln Gly Glu Asn Pro Pro Ser Phe Thr Arg
        930                 935                 940

Thr Asn Ser Asn Leu Pro Trp Ser Val Tyr Ala Arg Glu Lys Glu Arg
945                 950                 955                 960

Thr Ile

<210> SEQ ID NO 17
<211> LENGTH: 382
<212> TYPE: PRT
<213> ORGANISM: S. typhimirium

<400> SEQUENCE: 17

Met Thr Val Glu Lys Ser Val Val Phe Lys Ala Glu Gly Glu His Phe
1               5                   10                  15

Thr Asp Gln Lys Gly Asn Thr Ile Val Gly Ser Gly Ser Gly Gly Thr
                20                  25                  30

Thr Lys Tyr Phe Arg Ile Pro Ala Met Cys Thr Thr Ser Lys Gly Thr
            35                  40                  45

Ile Val Val Phe Ala Asp Ala Arg His Asn Thr Ala Ser Asp Gln Ser
50                  55                  60

Phe Ile Asp Thr Ala Ala Ala Arg Ser Thr Asp Gly Gly Lys Thr Trp
65                  70                  75                  80

Asn Lys Lys Ile Ala Ile Tyr Asn Asp Arg Val Asn Ser Lys Leu Ser
                85                  90                  95

Arg Val Met Asp Pro Thr Cys Ile Val Ala Asn Ile Gln Gly Arg Glu
            100                 105                 110

Thr Ile Leu Val Met Val Gly Lys Trp Asn Asn Asn Asp Lys Thr Trp
        115                 120                 125

Gly Ala Tyr Arg Asp Lys Ala Pro Asp Thr Asp Trp Asp Leu Val Leu
    130                 135                 140

Tyr Lys Ser Thr Asp Asp Gly Val Thr Phe Ser Lys Val Glu Thr Asn
145                 150                 155                 160

Ile His Asp Ile Val Thr Lys Asn Gly Thr Ile Ser Ala Met Leu Gly
                165                 170                 175
```

```
Gly Val Gly Ser Gly Leu Gln Leu Asn Asp Gly Lys Leu Val Phe Pro
            180                 185                 190

Val Gln Met Val Arg Thr Lys Asn Ile Thr Thr Val Leu Asn Thr Ser
        195                 200                 205

Phe Ile Tyr Ser Thr Asp Gly Ile Thr Trp Ser Leu Pro Ser Gly Tyr
    210                 215                 220

Cys Glu Gly Phe Gly Ser Glu Asn Asn Ile Ile Glu Phe Asn Ala Ser
225                 230                 235                 240

Leu Val Asn Asn Ile Arg Asn Ser Gly Leu Arg Arg Ser Phe Glu Thr
                245                 250                 255

Lys Asp Phe Gly Lys Thr Trp Thr Glu Phe Pro Pro Met Asp Lys Lys
            260                 265                 270

Val Asp Asn Arg Asn His Gly Val Gln Gly Ser Thr Ile Thr Ile Pro
                275                 280                 285

Ser Gly Asn Lys Leu Val Ala Ala His Ser Ser Ala Gln Asn Lys Asn
    290                 295                 300

Asn Asp Tyr Thr Arg Ser Asp Ile Ser Leu Tyr Ala His Asn Leu Tyr
305                 310                 315                 320

Ser Gly Glu Val Lys Leu Ile Asp Asp Phe Tyr Pro Lys Val Gly Asn
            325                 330                 335

Ala Ser Gly Ala Gly Tyr Ser Cys Leu Ser Tyr Arg Lys Asn Val Asp
            340                 345                 350

Lys Glu Thr Leu Tyr Val Val Tyr Glu Ala Asn Gly Ser Ile Glu Phe
            355                 360                 365

Gln Asp Leu Ser Arg His Leu Pro Val Ile Lys Ser Tyr Asn
    370                 375                 380
```